(12) United States Patent
Morgan et al.

(10) Patent No.: US 10,418,705 B2
(45) Date of Patent: *Sep. 17, 2019

(54) ELECTROMAGNETIC NAVIGATION ANTENNA ASSEMBLY AND ELECTROMAGNETIC NAVIGATION SYSTEM INCLUDING THE SAME

(71) Applicant: COVIDIEN LP, Mansfield, MA (US)

(72) Inventors: Sean M. Morgan, Golden Valley, MN (US); Lev A. Koyrakh, Plymouth, MN (US)

(73) Assignee: COVIDIEN LP, Mansfield, MA (US)

( * ) Notice: Subject to any disclaimer, the term of this patent is extended or adjusted under 35 U.S.C. 154(b) by 155 days.

This patent is subject to a terminal disclaimer.

(21) Appl. No.: 15/337,056

(22) Filed: Oct. 28, 2016

(65) Prior Publication Data

US 2018/0123248 A1  May 3, 2018

(51) Int. Cl.
*H01Q 7/00* (2006.01)
*H01Q 1/22* (2006.01)
*H01Q 21/28* (2006.01)
*H04B 5/00* (2006.01)
*A61B 34/00* (2016.01)
*H01Q 25/00* (2006.01)

(52) U.S. Cl.
CPC .............. *H01Q 7/00* (2013.01); *A61B 34/00* (2016.02); *H01Q 1/2208* (2013.01); *H01Q 21/28* (2013.01); *H04B 5/00* (2013.01); *H01Q 25/00* (2013.01)

(58) Field of Classification Search
CPC .............................. H01Q 7/00; H01Q 9/0457
USPC .......................................................... 343/742
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |

(Continued)

FOREIGN PATENT DOCUMENTS

| | | |
|---|---|---|
| CA | 964149 | 3/1975 |
| DE | 3508730 A1 | 9/1986 |

(Continued)

OTHER PUBLICATIONS

International Search Report and Written Opinion dated Feb. 19, 2018 and issued in corresponding International Application No. PCT/US2017/058406.

*Primary Examiner* — Hoang V Nguyen
*Assistant Examiner* — Awat M Salih

(57) ABSTRACT

An antenna assembly for radiating at least one electromagnetic field for electromagnetic navigation and an electromagnetic navigation system including such an antenna assembly are provided. The antenna assembly includes a substrate and a planar antenna including a trace that is deposited on the substrate and arranged in a plurality of loops. Respective distances between adjacent pairs of the loops increase in a direction from an innermost loop to an outermost loop.

10 Claims, 14 Drawing Sheets

(56) References Cited

U.S. PATENT DOCUMENTS

| | | |
|---|---|---|
| 3,073,310 A | 1/1963 | Mocarski |
| 3,109,588 A | 11/1963 | Polhemus et al. |
| 3,121,228 A | 2/1964 | Kalmus |
| 3,294,083 A | 12/1966 | Alderson |
| 3,367,326 A | 2/1968 | Frazier |
| 3,439,256 A | 4/1969 | Kahne et al. |
| 3,519,436 A | 7/1970 | Bauer et al. |
| 3,577,160 A | 5/1971 | White |
| 3,600,625 A | 8/1971 | Tsuneta et al. |
| 3,605,725 A | 9/1971 | Bentov |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,822,697 A | 7/1974 | Komiya |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,135,184 A | 1/1979 | Pruzick |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,249,167 A | 2/1981 | Purinton et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,308,530 A | 12/1981 | Kip et al. |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,341,385 A | 7/1982 | Doyle et al. |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,425,511 A | 1/1984 | Brosh |
| 4,431,005 A | 2/1984 | McCormick |
| 4,447,224 A | 5/1984 | DeCant, Jr. et al. |
| 4,447,462 A | 5/1984 | Tafuri et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,587,975 A | 5/1986 | Salo et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,695 A | 8/1987 | Macovski |
| 4,688,037 A | 8/1987 | Krieg |
| 4,696,544 A | 9/1987 | Costella |
| 4,697,595 A | 10/1987 | Breyer et al. |
| 4,701,049 A | 10/1987 | Beckman et al. |
| 4,704,602 A | 11/1987 | Asbrink |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,726,355 A | 2/1988 | Okada |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,784,117 A | 11/1988 | Miyazaki |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |

(56) References Cited

U.S. PATENT DOCUMENTS

| | | |
|---|---|---|
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |
| 5,013,317 A | 5/1991 | Cole et al. |
| 5,016,639 A | 5/1991 | Allen |
| 5,017,139 A | 5/1991 | Mushabac |
| 5,023,102 A | 6/1991 | Given, Jr. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| RE33,662 E | 8/1991 | Blair et al. |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,462 A | 12/1991 | Chau |
| 5,078,140 A | 1/1992 | Kwoh |
| 5,079,699 A | 1/1992 | Tuy et al. |
| 5,082,286 A | 1/1992 | Ryan et al. |
| 5,086,401 A | 2/1992 | Glassman et al. |
| 5,088,928 A | 2/1992 | Chan |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,129,654 A | 7/1992 | Bogner |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,188,368 A | 2/1993 | Ryan |
| 5,190,059 A | 3/1993 | Fabian et al. |
| 5,190,285 A | 3/1993 | Levy et al. |
| 5,193,106 A | 3/1993 | DeSena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,203,337 A | 4/1993 | Feldman |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,722 A | 11/1993 | Hedengren et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,307,816 A | 5/1994 | Hashimoto et al. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,327,889 A | 7/1994 | Imran |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,347,289 A | 9/1994 | Elhardt |
| 5,353,795 A | 10/1994 | Souza et al. |
| 5,353,800 A | 10/1994 | Pohndorf et al. |
| 5,353,807 A | 10/1994 | DeMarco |
| 5,357,253 A | 10/1994 | Van Etten et al. |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,376,795 A | 12/1994 | Hasegawa et al. |
| 5,377,678 A | 1/1995 | Dumoulin et al. |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,073 A | 2/1995 | Imran |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,321 A | 3/1995 | Houser et al. |
| 5,397,329 A | 3/1995 | Allen |
| 5,398,684 A | 3/1995 | Hardy |
| 5,398,691 A | 3/1995 | Martin et al. |
| 5,399,146 A | 3/1995 | Nowacki et al. |
| 5,400,384 A | 3/1995 | Fernandes et al. |
| 5,400,771 A | 3/1995 | Pirak et al. |
| 5,402,801 A | 4/1995 | Taylor |
| 5,405,346 A | 4/1995 | Grundy et al. |
| 5,408,409 A | 4/1995 | Glassman et al. |
| 5,409,000 A | 4/1995 | Imran |

(56) References Cited

U.S. PATENT DOCUMENTS

| | | |
|---|---|---|
| 5,412,414 A | 5/1995 | Ast et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| 5,435,573 A | 7/1995 | Oakford |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,447,156 A | 9/1995 | Dumoulin et al. |
| 5,448,610 A | 9/1995 | Yamamoto et al. |
| 5,453,686 A | 9/1995 | Anderson |
| 5,456,254 A | 10/1995 | Pietroski et al. |
| 5,456,664 A | 10/1995 | Heinzelman et al. |
| 5,456,689 A | 10/1995 | Kresch et al. |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,472,441 A | 12/1995 | Edwards et al. |
| 5,476,100 A | 12/1995 | Galel |
| 5,476,495 A | 12/1995 | Kordis et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,492,131 A | 2/1996 | Galel |
| 5,492,713 A | 2/1996 | Sommermeyer |
| 5,493,517 A | 2/1996 | Frazier |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,515,853 A | 5/1996 | Smith et al. |
| 5,517,990 A | 5/1996 | Kalfas et al. |
| 5,520,059 A | 5/1996 | Garshelis |
| 5,522,814 A | 6/1996 | Bemaz |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,545,200 A | 8/1996 | West et al. |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,033 A | 12/1996 | Yeung |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,599,305 A | 2/1997 | Hermann et al. |
| 5,600,330 A | 2/1997 | Blood |
| 5,603,318 A | 2/1997 | Heilbrun et al. |
| 5,606,975 A | 3/1997 | Liang et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,620,734 A | 4/1997 | Wesdorp et al. |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,634 A | 6/1997 | Kordis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,646,525 A | 7/1997 | Gilboa |
| 5,647,361 A | 7/1997 | Damadian |
| 5,651,047 A | 7/1997 | Moorman et al. |
| 5,660,865 A | 8/1997 | Pedersen et al. |
| 5,662,108 A | 9/1997 | Budd et al. |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,165 A | 10/1997 | Lewis et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,701,898 A | 12/1997 | Adam et al. |
| 5,702,406 A | 12/1997 | Vilsmeier et al. |
| 5,711,299 A | 1/1998 | Manwaring et al. |
| 5,713,369 A | 2/1998 | Tao et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |

(56) References Cited

U.S. PATENT DOCUMENTS

| | | |
|---|---|---|
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | McGee et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,050 A | 7/1998 | Chen et al. |
| 5,776,064 A | 7/1998 | Kalfas et al. |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,084 A | 9/1998 | Olson |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Cheng et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | McCarty et al. |
| 5,957,844 A | 9/1999 | Dekel et al. |
| 5,966,090 A | 10/1999 | McEwan |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |
| 6,096,036 A | 8/2000 | Bowe et al. |
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |

(56) References Cited

U.S. PATENT DOCUMENTS

| | | |
|---|---|---|
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,179,809 B1 | 1/2001 | Khairkhahan et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,208,884 B1 | 3/2001 | Kumar et al. |
| 6,210,362 B1 | 4/2001 | Ponzi |
| 6,211,666 B1 | 4/2001 | Acker |
| 6,213,995 B1 | 4/2001 | Steen et al. |
| 6,213,998 B1 | 4/2001 | Shen et al. |
| 6,216,027 B1 | 4/2001 | Willis et al. |
| 6,216,029 B1 | 4/2001 | Paltieli |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,245,020 B1 | 6/2001 | Moore et al. |
| 6,246,231 B1 | 6/2001 | Ashe |
| 6,246,784 B1 | 6/2001 | Summers et al. |
| 6,246,898 B1 | 6/2001 | Vesely et al. |
| 6,246,899 B1 | 6/2001 | Chia et al. |
| 6,248,074 B1 | 6/2001 | Ohno et al. |
| 6,253,770 B1 | 7/2001 | Acker et al. |
| 6,259,942 B1 | 7/2001 | Westermann et al. |
| 6,264,654 B1 | 7/2001 | Swartz et al. |
| 6,272,371 B1 | 8/2001 | Shlomo |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,331,116 B1 | 12/2001 | Kaufman et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,346,940 B1 | 2/2002 | Fukunaga |
| 6,351,513 B1 | 2/2002 | Bani-Hashemi et al. |
| 6,351,659 B1 | 2/2002 | Vilsmeier |
| 6,366,799 B1 | 4/2002 | Acker et al. |
| 6,373,240 B1 | 4/2002 | Govari |
| 6,380,732 B1 | 4/2002 | Gilboa |
| 6,381,485 B1 | 4/2002 | Hunter et al. |
| 6,383,144 B1 | 5/2002 | Mooney et al. |
| 6,405,072 B1 | 6/2002 | Cosman |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,473,635 B1 | 10/2002 | Rasche |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,477 B1 | 12/2002 | Govari et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,517,534 B1 | 2/2003 | McGovern et al. |
| 6,527,443 B1 | 3/2003 | Vilsmeier et al. |
| 6,551,325 B2 | 4/2003 | Neubauer et al. |
| 6,558,333 B2 | 5/2003 | Gilboa et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,585,763 B1 | 7/2003 | Keilman et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,816 B2 | 2/2004 | Aylward et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,702,780 B1 | 3/2004 | Gilboa et al. |
| 6,706,041 B1 | 3/2004 | Costantino |
| 6,711,429 B1 | 3/2004 | Gilboa et al. |
| 6,735,465 B2 | 5/2004 | Panescu |
| 6,751,492 B2 | 6/2004 | Ben-Haim |
| 6,770,070 B1 | 8/2004 | Balbierz |
| 6,788,967 B2 | 9/2004 | Ben-Haim et al. |
| 6,796,963 B2 | 9/2004 | Carpenter et al. |
| 6,810,281 B2 | 10/2004 | Brock et al. |
| 6,833,814 B2 | 12/2004 | Gilboa et al. |
| 6,887,236 B2 | 5/2005 | Gilboa |
| 6,947,788 B2 | 9/2005 | Gilboa et al. |
| 6,976,013 B1 | 12/2005 | Mah |
| 6,995,729 B2 | 2/2006 | Govari et al. |
| 6,996,430 B1 | 2/2006 | Gilboa et al. |
| 7,015,859 B2 | 3/2006 | Anderson |
| 7,033,325 B1 | 4/2006 | Sullivan |
| 7,158,754 B2 | 1/2007 | Anderson |
| 7,176,936 B2 | 2/2007 | Sauer et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,420,468 B2 | 9/2008 | Fabian et al. |
| 7,497,029 B2 | 3/2009 | Plassky et al. |
| 7,505,809 B2 | 3/2009 | Strommer et al. |

(56) References Cited

U.S. PATENT DOCUMENTS

| | | |
|---|---|---|
| 7,517,318 B2 | 4/2009 | Altmann et al. |
| 7,536,218 B2 | 5/2009 | Govari et al. |
| 7,555,330 B2 | 6/2009 | Gilboa et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,652,578 B2 | 1/2010 | Braun et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,782,046 B2 | 8/2010 | Anderson |
| 7,782,189 B2 | 8/2010 | Spoonhower et al. |
| 7,784,468 B2 | 8/2010 | Fabian et al. |
| 7,831,076 B2 | 11/2010 | Altmann et al. |
| 7,905,827 B2 | 3/2011 | Uchiyama et al. |
| 7,912,662 B2 | 3/2011 | Zuhars et al. |
| 7,969,143 B2 | 6/2011 | Gilboa |
| 8,692,707 B2 | 4/2014 | Lee et al. |
| 9,575,140 B2 | 2/2017 | Zur |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2001/0038705 A1 | 11/2001 | Rubbert et al. |
| 2002/0022837 A1 | 2/2002 | Mazzocchi et al. |
| 2002/0045916 A1 | 4/2002 | Gray et al. |
| 2002/0045919 A1 | 4/2002 | Johansson-Ruden et al. |
| 2002/0065461 A1 | 5/2002 | Cosman |
| 2002/0082498 A1 | 6/2002 | Wendt et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0143324 A1 | 10/2002 | Edwards |
| 2002/0165448 A1 | 11/2002 | Ben-Haim et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0099390 A1 | 5/2003 | Zeng et al. |
| 2003/0142753 A1 | 7/2003 | Gunday |
| 2003/0144658 A1 | 7/2003 | Schwartz et al. |
| 2003/0160721 A1 | 8/2003 | Gilboa et al. |
| 2003/0216639 A1 | 11/2003 | Gilboa et al. |
| 2004/0006268 A1 | 1/2004 | Gilboa et al. |
| 2004/0015049 A1 | 1/2004 | Zaar |
| 2004/0019350 A1 | 1/2004 | O'Brien et al. |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0122310 A1 | 6/2004 | Lim |
| 2004/0138548 A1 | 7/2004 | Strommer et al. |
| 2004/0143317 A1 | 7/2004 | Stinson et al. |
| 2004/0169509 A1 | 9/2004 | Czipott et al. |
| 2004/0215181 A1 | 10/2004 | Christopherson et al. |
| 2004/0249267 A1 | 12/2004 | Gilboa |
| 2004/0254454 A1 | 12/2004 | Kockro |
| 2005/0018885 A1 | 1/2005 | Chen et al. |
| 2005/0027193 A1 | 2/2005 | Mitschke et al. |
| 2005/0033149 A1 | 2/2005 | Strommer et al. |
| 2005/0059890 A1 | 3/2005 | Deal et al. |
| 2005/0085715 A1 | 4/2005 | Dukesherer et al. |
| 2005/0085720 A1 | 4/2005 | Jascob et al. |
| 2005/0090818 A1 | 4/2005 | Pike et al. |
| 2005/0107687 A1 | 5/2005 | Anderson |
| 2005/0107688 A1 | 5/2005 | Strommer |
| 2005/0119527 A1 | 6/2005 | Banik et al. |
| 2005/0182295 A1 | 8/2005 | Soper et al. |
| 2005/0197566 A1 | 9/2005 | Strommer et al. |
| 2005/0222793 A1 | 10/2005 | Lloyd et al. |
| 2005/0272971 A1 | 12/2005 | Ohnishi et al. |
| 2006/0015126 A1 | 1/2006 | Sher |
| 2006/0025677 A1 | 2/2006 | Verard et al. |
| 2006/0036151 A1 | 2/2006 | Ferre et al. |
| 2006/0058647 A1 | 3/2006 | Strommer et al. |
| 2006/0064006 A1 | 3/2006 | Strommer et al. |
| 2006/0079759 A1 | 4/2006 | Vaillant et al. |
| 2006/0084867 A1 | 4/2006 | Tremblay et al. |
| 2006/0116575 A1 | 6/2006 | Willis |
| 2006/0149134 A1 | 7/2006 | Soper et al. |
| 2006/0181271 A1 | 8/2006 | Lescourret |
| 2006/0208725 A1 | 9/2006 | Tapson |
| 2006/0241396 A1 | 10/2006 | Fabian et al. |
| 2006/0241399 A1 | 10/2006 | Fabian |
| 2006/0262029 A1 | 11/2006 | Anderson |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167804 A1 | 7/2007 | Park et al. |
| 2007/0167806 A1 | 7/2007 | Wood et al. |
| 2007/0225553 A1 | 9/2007 | Shahidi |
| 2007/0232898 A1 | 10/2007 | Huynh et al. |
| 2007/0265639 A1 | 11/2007 | Danek et al. |
| 2007/0287901 A1 | 12/2007 | Strommer et al. |
| 2008/0008368 A1 | 1/2008 | Matsumoto |
| 2008/0018468 A1 | 1/2008 | Volpi et al. |
| 2008/0033452 A1 | 2/2008 | Vetter et al. |
| 2008/0086051 A1 | 4/2008 | Voegele |
| 2008/0097154 A1 | 4/2008 | Makower et al. |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |
| 2008/0284554 A1 | 11/2008 | Schroeder et al. |
| 2009/0027258 A1 | 1/2009 | Stayton |
| 2009/0082665 A1 | 3/2009 | Anderson |
| 2009/0182224 A1 | 7/2009 | Shmarak et al. |
| 2009/0189820 A1 | 7/2009 | Saito et al. |
| 2009/0318797 A1 | 12/2009 | Hadani |
| 2010/0301841 A1 | 12/2010 | Anderson |
| 2011/0085720 A1 | 4/2011 | Barak et al. |
| 2012/0007787 A1 | 1/2012 | Schantz et al. |
| 2013/0140369 A1* | 6/2013 | Dokai ............... H01Q 1/2208 235/492 |
| 2014/0148692 A1 | 5/2014 | Hartmann et al. |

(56) References Cited

U.S. PATENT DOCUMENTS

| | | | | |
|---|---|---|---|---|
| 2014/0375524 | A1* | 12/2014 | Nago | H01Q 7/00 343/866 |
| 2015/0035697 | A1 | 2/2015 | Cho | |
| 2015/0130291 | A1* | 5/2015 | Lim | H01Q 1/2225 307/104 |
| 2016/0028159 | A1* | 1/2016 | Moon | H04B 5/0075 343/749 |

FOREIGN PATENT DOCUMENTS

| | | |
|---|---|---|
| DE | 3520782 A1 | 12/1986 |
| DE | 3717871 A1 | 12/1988 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0655138 B1 | 5/1995 |
| EP | 0796633 A1 | 9/1997 |
| EP | 0 829 229 A1 | 3/1998 |
| EP | 0894473 A2 | 2/1999 |
| EP | 0908146 A2 | 4/1999 |
| EP | 0 922 966 A2 | 6/1999 |
| EP | 0930046 A2 | 7/1999 |
| EP | 1078644 A1 | 2/2001 |
| EP | 2096523 A1 | 9/2009 |
| FR | 2618211 A1 | 1/1989 |
| GB | 2094590 A | 9/1982 |
| GB | 2164856 A | 4/1986 |
| GB | 2197078 A | 5/1988 |
| JP | 03-267054 A | 11/1991 |
| JP | 06194639 A | 7/1994 |
| JP | 3025752 B2 | 3/2000 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 95/09562 A1 | 4/1995 |
| WO | 9605768 A1 | 2/1996 |
| WO | 96/11624 A2 | 4/1996 |
| WO | 96/32059 A1 | 10/1996 |
| WO | 96/41119 A1 | 12/1996 |
| WO | 97/00011 A1 | 1/1997 |
| WO | 97/00054 A1 | 1/1997 |
| WO | 97/00058 A1 | 1/1997 |
| WO | 97/00059 A1 | 1/1997 |
| WO | 97/00308 A1 | 1/1997 |
| WO | 97/02650 A1 | 1/1997 |
| WO | 97/25101 A2 | 7/1997 |
| WO | 97/29682 A1 | 8/1997 |
| WO | 97/29684 A1 | 8/1997 |
| WO | 97/29685 A1 | 8/1997 |
| WO | 97/29701 A1 | 8/1997 |
| WO | 97/29709 A1 | 8/1997 |
| WO | 97/36143 A1 | 10/1997 |
| WO | 97/36192 A1 | 10/1997 |
| WO | 97/42517 A1 | 11/1997 |
| WO | 97/44089 A1 | 11/1997 |
| WO | 97/49453 A1 | 12/1997 |
| WO | 98/00034 A2 | 1/1998 |
| WO | 98/08554 A1 | 3/1998 |
| WO | 98/11840 A1 | 3/1998 |
| WO | 98/29032 A1 | 7/1998 |
| WO | 98/35720 A2 | 8/1998 |
| WO | 98/38908 A1 | 9/1998 |
| WO | 98/48722 A1 | 11/1998 |
| WO | 99/15097 A2 | 4/1999 |
| WO | 99/16350 A1 | 4/1999 |
| WO | 99/21498 A1 | 5/1999 |
| WO | 99/23956 A1 | 5/1999 |
| WO | 99/26549 A1 | 6/1999 |
| WO | 99/26826 A2 | 6/1999 |
| WO | 99/27839 A2 | 6/1999 |
| WO | 99/29253 A1 | 6/1999 |
| WO | 9930777 A1 | 6/1999 |
| WO | 99/32033 A1 | 7/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 9955415 A1 | 11/1999 |
| WO | 99/60939 A1 | 12/1999 |
| WO | 00/06701 A1 | 2/2000 |
| WO | 00/16684 A1 | 3/2000 |
| WO | 0010456 A1 | 3/2000 |
| WO | 00/35531 A1 | 6/2000 |
| WO | 01/06917 A1 | 2/2001 |
| WO | 0112057 A1 | 2/2001 |
| WO | 01/30437 A1 | 5/2001 |
| WO | 0167035 A1 | 9/2001 |
| WO | 01/87136 A2 | 11/2001 |
| WO | 01/91842 A1 | 12/2001 |
| WO | 02/64011 A2 | 8/2002 |
| WO | 02/70047 A1 | 9/2002 |
| WO | 03/86498 A2 | 10/2003 |
| WO | 2004/023986 A1 | 3/2004 |
| WO | 2006/116597 A2 | 11/2006 |
| WO | 2015164171 A1 | 10/2015 |

* cited by examiner

ELECTROMAGNETIC NAVIGATION ANTENNA ASSEMBLY AND ELECTROMAGNETIC NAVIGATION SYSTEM INCLUDING THE SAME

BACKGROUND

Technical Field

The present disclosure relates to antenna assemblies for electromagnetic navigation and methods for designing such antenna assemblies. More particularly, the present disclosure relates to antenna assemblies for radiating electromagnetic fields for electromagnetic navigation, electromagnetic navigation systems including such antenna assemblies, and computer-implemented methods of designing such antenna assemblies.

Discussion of Related Art

Electromagnetic (EM) navigation (EMN) has helped expand medical imaging, diagnosis, prognosis, and treatment capabilities by enabling a location and/or an orientation of a medical device to be accurately determined while the device is within the body of a patient. One example of a medical procedure in which EMN is employed is ELECTROMAGNETIC NAVIGATION BRONCHOSCOPY® (ENB™), which includes a planning phase and a navigation phase. During the planning phase, a computed tomography (CT) scan of the chest of the patient is used to generate a virtual three-dimensional bronchial map of the patient and a planned pathway for the navigation phase. During the navigation phase, an antenna assembly radiates an electromagnetic field throughout the chest of the patient, a practitioner inserts into the airway of the patient an electromagnetic sensor that senses the radiated electromagnetic field, and a computing device determines a location and/or an orientation (e.g., relative to the planned pathway) of the electromagnetic sensor based on characteristics of the sensed electromagnetic field.

To enable accurate determination of sensor location and/or orientation, a detailed mapping of electromagnetic field measurements at respective sensor locations is generated. Generating such a mapping, however, requires taking precise electromagnetic field measurements at many (for example, hundreds of thousands or more) locations within the expected electromagnetic volume, which is a laborious and time-consuming process that, in some cases, requires expensive machines.

The burden of generating electromagnetic field mappings increases in circumstances where multiple antenna assemblies are employed. For example, in order to enable an electromagnetic sensor to reach deeper portions of the body of the patient, and/or remain within the body during subsequent medical procedures without interfering with additional medical devices, it may be desirable to employ a small electromagnetic sensor, such as a single-coil electromagnetic sensor. However, to employ a small electromagnetic sensor for EMN while maintaining the ability to determine multiple (for example, six) degrees of freedom of the sensor, multiple antenna assemblies may be required to increase the number of radiated electromagnetic fields to be sensed. In such a case, the above-noted exhaustive mapping procedure may need to be conducted for each antenna assembly design. Moreover, given potential variations from manufacturing, the mapping procedure may even need to be completed for each instance of a specific antenna assembly design (i.e., each individual antenna assembly manufactured).

Given the foregoing, a need exists for improved electromagnetic navigation antenna assemblies and methods for designing such antenna assemblies.

SUMMARY

According to an aspect of the present disclosure, an antenna assembly for radiating at least one electromagnetic field for electromagnetic navigation is provided. The antenna assembly includes a substrate and a planar antenna including a trace that is deposited on the substrate and arranged in multiple loops. Respective distances between adjacent pairs of the loops increase in a direction from an innermost loop to an outermost loop.

In another aspect of the present disclosure, each of the loops includes multiple straight linear portions and multiple vertices. For example, in some aspects, each of the loops includes four straight linear portions and four vertices.

In a further aspect of the present disclosure, each of the vertices is disposed along one of four diagonal lines that bisect four respective vertices of a seed rectangle corresponding to the planar antenna.

In yet another aspect of the present disclosure, the antenna assembly further includes a connector having at least two terminals, and the trace has two ends that are coupled to the two terminals, respectively.

In another aspect of the present disclosure, the antenna assembly includes multiple planar antennas, and each of the multiple planar antennas includes a respective trace deposited on the substrate and arranged in a respective set of loops. For each of the planar antennas, respective distances between adjacent pairs of the loops of the respective planar antenna increase in a direction from an innermost loop to an outermost loop.

In another aspect of the present disclosure, the substrate includes multiple layers and the planar antenna and each of the multiple planar antennas is deposited on a respective one of the layers.

In another aspect of the present disclosure, each of the planar antennas includes a same number of loops.

In another aspect of the present disclosure, each of the loops includes multiple straight linear portions and multiple vertices.

In another aspect of the present disclosure, the planar antennas have respective centroids, with respect to a plane of the substrate, that are disposed in respective positions that are distinct from one another.

According to another aspect of the present disclosure, an electromagnetic navigation system is provided. The system includes an antenna assembly, an alternating current (AC) current driver that drives the antenna assembly, a catheter, an electromagnetic sensor, a processor, and a memory. The antenna assembly includes a substrate and a planar antenna and is configured to radiate an electromagnetic field. The planar antenna includes a trace deposited on the substrate and arranged in multiple loops. Respective distances between adjacent pairs of the loops increase in a direction from an innermost one of the loops to an outermost one of the loops. The electromagnetic sensor is affixed to the catheter and is configured to receive a signal based on the radiated electromagnetic field. The memory includes instructions that, when executed by the processor, cause the processor to calculate a location and/or an orientation of the electromagnetic sensor based on the received signal.

In another aspect of the present disclosure, each of the loops includes multiple straight linear portions and multiple vertices. For example, in some aspects each of the loops includes four straight linear portions and four vertices.

In a further aspect of the present disclosure, each of the vertices is disposed along one of four diagonal lines that bisect four respective vertices of a seed rectangle corresponding to the planar antenna.

In yet another aspect of the present disclosure, the antenna assembly further includes a connector having at least two terminals, and the trace has two ends that are coupled to the two terminals, respectively.

In another aspect of the present disclosure, the antenna assembly includes multiple planar antennas, each of the planar antennas including a respective trace deposited on the substrate and arranged in a respective set of loops. For each of the planar antennas, respective distances between adjacent pairs of the loops increase in a direction from an innermost one of the loops to an outermost one of the loops of the respective planar antenna.

In another aspect of the present disclosure, the substrate includes multiple layers and each of the planar antennas is deposited on a respective layer of the multiple layers.

In another aspect of the present disclosure, each of the planar antennas includes a same number of loops.

In another aspect of the present disclosure, each of the loops of each of the planar antennas includes multiple straight linear portions and multiple vertices.

In another aspect of the present disclosure, the multiple planar antennas have multiple centroids, respectively, with respect to a plane of the substrate that are disposed in respective positions that are distinct from one another.

According to another aspect of the present disclosure, an antenna assembly for radiating multiple electromagnetic fields for electromagnetic navigation is provided. The antenna assembly includes a substrate and multiple groups of planar antennas. The substrate includes a multiple layers, and each of the planar antennas includes a respective trace that is deposited on a respective layer of the multiple layers and is arranged in a respective number of loops. Each of the groups of planar antennas includes a first planar antenna, a second planar antenna, and a third planar antenna. For each of the groups of planar antennas: (1) an innermost loop of the first planar antenna has a first linear portion and a second linear portion approximately perpendicular to the first linear portion, (2) an innermost loop of the second planar antenna has a first linear portion and a second linear portion approximately perpendicular to the first linear portion and longer than the first linear portion, (3) an innermost loop of the third planar antenna has a first linear portion and a second linear portion approximately perpendicular to the first linear portion and longer than the first linear portion, (4) the first linear portion of the innermost loop of the second planar antenna is approximately parallel to the first linear portion of the innermost loop of the first planar antenna, and (5) the first linear portion of the innermost loop of the third planar antenna is approximately parallel to the second linear portion of the innermost loop of the first planar antenna.

In another aspect of the present disclosure, for each of the planar antennas, respective distances between adjacent loops of the multiple loops increase in a direction from an innermost loop of the multiple loops to an outermost loop of the multiple loops.

In a further aspect of the present disclosure, the respective innermost loops of the first planar antennas of each group are positioned, on the respective layers of the multiple layers, at respective angles that are distinct from one another.

In yet another aspect of the present disclosure, each of the multiple loops includes multiple straight linear portions and multiple vertices.

In another aspect of the present disclosure, for each planar antenna of the multiple planar antennas, each of the multiple vertices is disposed along one of four diagonal lines that bisect four respective vertices of a seed rectangle corresponding to the respective planar antenna of the multiple planar antennas.

In a further aspect of the present disclosure, respective outermost vertices of the multiple vertices of the multiple planar antennas are distanced from an edge of the substrate by not more than a predetermined threshold.

In yet another aspect of the present disclosure, the planar antennas have respective centroids, with respect to a plane of the substrate, that are distinct from one another.

In another aspect of the present disclosure, each of the planar antennas includes a same number of loops.

In a further aspect of the present disclosure, the number of groups of planar antennas is at least three.

In still another aspect of the present disclosure, the antenna assembly further includes a connector having multiple terminals, and each of the respective traces of the multiple planar antennas is coupled to a respective terminal of the multiple terminals.

According to another aspect of the present disclosure, an electromagnetic navigation system is provided that includes an antenna assembly, a catheter, an electromagnetic sensor, a processor, and a memory. The antenna assembly is configured to radiate electromagnetic fields and includes a substrate and multiple groups of planar antennas. The substrate includes multiple layers, and each of the planar antennas includes a respective trace that is deposited on a respective layer of the multiple layers and is arranged in a respective number of loops. Each of the groups of planar antennas includes a first planar antenna, a second planar antenna, and a third planar antenna. For each of the multiple groups of planar antennas: (1) an innermost loop of the first planar antenna has a first linear portion and a second linear portion approximately perpendicular to the first linear portion, (2) an innermost loop of the second planar antenna has a first linear portion and a second linear portion approximately perpendicular to the first linear portion and longer than the first linear portion, (3) an innermost loop of the third planar antenna has a first linear portion and a second linear portion approximately perpendicular to the first linear portion and longer than the first linear portion, (4) the first linear portion of the innermost loop of the second planar antenna is approximately parallel to the first linear portion of the innermost loop of the first planar antenna, and (5) the first linear portion of the innermost loop of the third planar antenna is approximately parallel to the second linear portion of the innermost loop of the first planar antenna. The electromagnetic sensor is affixed to the catheter and is configured to receive one or more signals based on the radiated electromagnetic fields. The memory includes instructions that, when executed by the processor, cause the processor to calculate a location and/or an orientation of the electromagnetic sensor based on the received signal(s).

In another aspect of the present disclosure, for each of the planar antennas, respective distances between adjacent loops of the multiple loops increase in a direction from an innermost loop of the multiple loops to an outermost loop of the multiple loops.

In a further aspect of the present disclosure, the respective innermost loops of the first planar antennas of each group are positioned, on the respective layers of the multiple layers, at respective angles that are distinct from one another.

In yet another aspect of the present disclosure, each of the multiple loops includes multiple straight linear portions and multiple vertices.

In another aspect of the present disclosure, for each planar antenna of the multiple planar antennas, each of the multiple vertices is disposed along one of four diagonal lines that bisect four respective vertices of a seed rectangle corresponding to the respective planar antenna of the multiple planar antennas.

In a further aspect of the present disclosure, respective outermost vertices of the multiple vertices of the multiple planar antennas are distanced from an edge of the substrate by not more than a predetermined threshold.

In yet another aspect of the present disclosure, the multiple planar antennas have multiple respective centroids, with respect to a plane of the substrate, that are distinct from one another.

In another aspect of the present disclosure, each of the planar antennas includes a same number of loops.

In a further aspect of the present disclosure, the number of groups of planar antennas is at least three.

In yet another aspect of the present disclosure, the electromagnetic navigation system further includes a connector that has multiple terminals, and each of the respective traces of the multiple planar antennas is coupled to a respective terminal of the multiple terminals.

According to another aspect of the present disclosure, a computer-implemented method of designing an antenna assembly for radiating an electromagnetic field for electromagnetic navigation is provided. The method includes computing, relative to a coordinate system of a substrate that has a boundary, multiple diagonal lines based on a seed rectangle that has multiple vertices, respectively. The multiple diagonal lines bisect the multiple vertices of the seed rectangle, respectively, and extend from the multiple vertices of the seed rectangle, respectively, to the boundary. The method also includes, for each of the multiple diagonal lines: (1) determining multiple distances between multiple adjacent pairs of planar antenna vertices, respectively, to be positioned along the respective diagonal line, wherein the multiple distances increase in a direction from the respective vertex of the seed rectangle to the boundary, and (2) positioning the planar antenna vertices along the respective diagonal line based on the determined multiple distances. A planar antenna layout is generated by interconnecting the planar antenna vertices by way of respective straight linear portions to form multiple loops that sequentially traverse each of the multiple diagonal lines.

In another aspect of the present disclosure, the multiple distances are determined based at least in part on a predetermined number of loops of the planar antenna.

In a further aspect of the present disclosure, the multiple distances are determined based at least in part on a predetermined minimum spacing between adjacent vertices and/or a predetermined minimum spacing between adjacent traces.

In yet another aspect of the present disclosure, the substrate has multiple layers and the method further includes generating multiple planar antenna layouts corresponding to the multiple layers, respectively.

In another aspect of the present disclosure, the computer-implemented method further includes adding to the planar antenna layout multiple straight linear portions routed from at least two of the planar antenna vertices to a connector location with respect to the coordinate system of the substrate.

In a further aspect of the present disclosure, the computer-implemented method further includes computing, for each of the multiple diagonal lines, a layout distance between the respective vertex of the seed rectangle and the boundary along the respective diagonal line, and the determining of the multiple distances between the multiple pairs of adjacent planar antenna vertices, respectively, is based at least in part on the computed layout distance.

In yet another aspect of the present disclosure, each of the multiple loops includes multiple of the straight linear portions and multiple of the planar antenna vertices.

In another aspect of the present disclosure, an outermost planar antenna vertex of the multiple planar antenna vertices is distanced from the boundary of the substrate by not more than a predetermined threshold.

In a further aspect of the present disclosure, the computer-implemented method further includes exporting data corresponding to the generated planar antenna layout to a circuit board routing tool and/or a circuit board manufacturing tool.

In yet another aspect of the present disclosure, the computer-implemented method further includes exporting data corresponding to the generated planar antenna layout to an electromagnetic simulation tool and simulating, based on the exported data, an electromagnetic field based on superposition of multiple electromagnetic field components from the multiple straight linear portions of the planar antenna layout, respectively.

According to another aspect of the present disclosure, a non-transitory computer-readable medium is provided, which stores instructions that, when executed by a processor, cause the processor to perform a method of designing an antenna assembly for radiating an electromagnetic field for electromagnetic navigation. The method includes computing, relative to a coordinate system of a substrate having a boundary, multiple diagonal lines based on a seed rectangle that has multiple vertices, respectively. The multiple diagonal lines bisect the multiple vertices of the seed rectangle, respectively, and extend from the multiple vertices of the seed rectangle, respectively, to the boundary. The method further includes, for each of the multiple diagonal lines, (1) determining multiple respective distances between multiple adjacent pairs of planar antenna vertices to be positioned along the respective diagonal line, and (2) positioning the planar antenna vertices along the respective diagonal line based on the determined multiple distances. The multiple distances increase in a direction from the respective vertex of the seed rectangle to the boundary. A planar antenna layout is generated by interconnecting the planar antenna vertices by way of respective straight linear portions to form multiple loops that sequentially traverse each of the multiple diagonal lines.

In another aspect of the present disclosure, the multiple distances are determined based at least in part on a predetermined number of loops of the planar antenna.

In a further aspect of the present disclosure, the multiple distances are determined based at least in part on a predetermined minimum spacing between adjacent vertices and/or a predetermined minimum spacing between adjacent traces.

In yet another aspect of the present disclosure, the substrate has multiple layers and the method further includes generating multiple planar antenna layouts that correspond to the multiple layers, respectively.

In another aspect of the present disclosure, the method further includes adding to the planar antenna layout multiple straight linear portions routed from at least two of the planar antenna vertices to a connector location with respect to the coordinate system of the substrate.

In a further aspect of the present disclosure, the method further comprises, for each of the plurality of diagonal lines, computing a layout distance between the respective vertex of the seed rectangle and the boundary along the respective diagonal line, and the determining of the multiple distances between the multiple pairs of adjacent planar antenna vertices, respectively, is based at least in part on the computed layout distance.

In yet another aspect of the present disclosure, each of the multiple loops includes multiple of the straight linear portions and multiple of the planar antenna vertices.

In another aspect of the present disclosure, an outermost planar antenna vertex of the multiple planar antenna vertices is distanced from the boundary of the substrate by not more than a predetermined threshold.

In a further aspect of the present disclosure, the method further includes exporting data corresponding to the generated planar antenna layout to a circuit board routing tool and/or a circuit board manufacturing tool.

In yet another aspect of the present disclosure, the method further includes exporting data corresponding to the generated planar antenna layout to an electromagnetic simulation tool and simulating, based on the exported data, an electromagnetic field based on superposition of multiple electromagnetic field components from the multiple straight linear portions of the planar antenna layout, respectively.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

Figure 1:
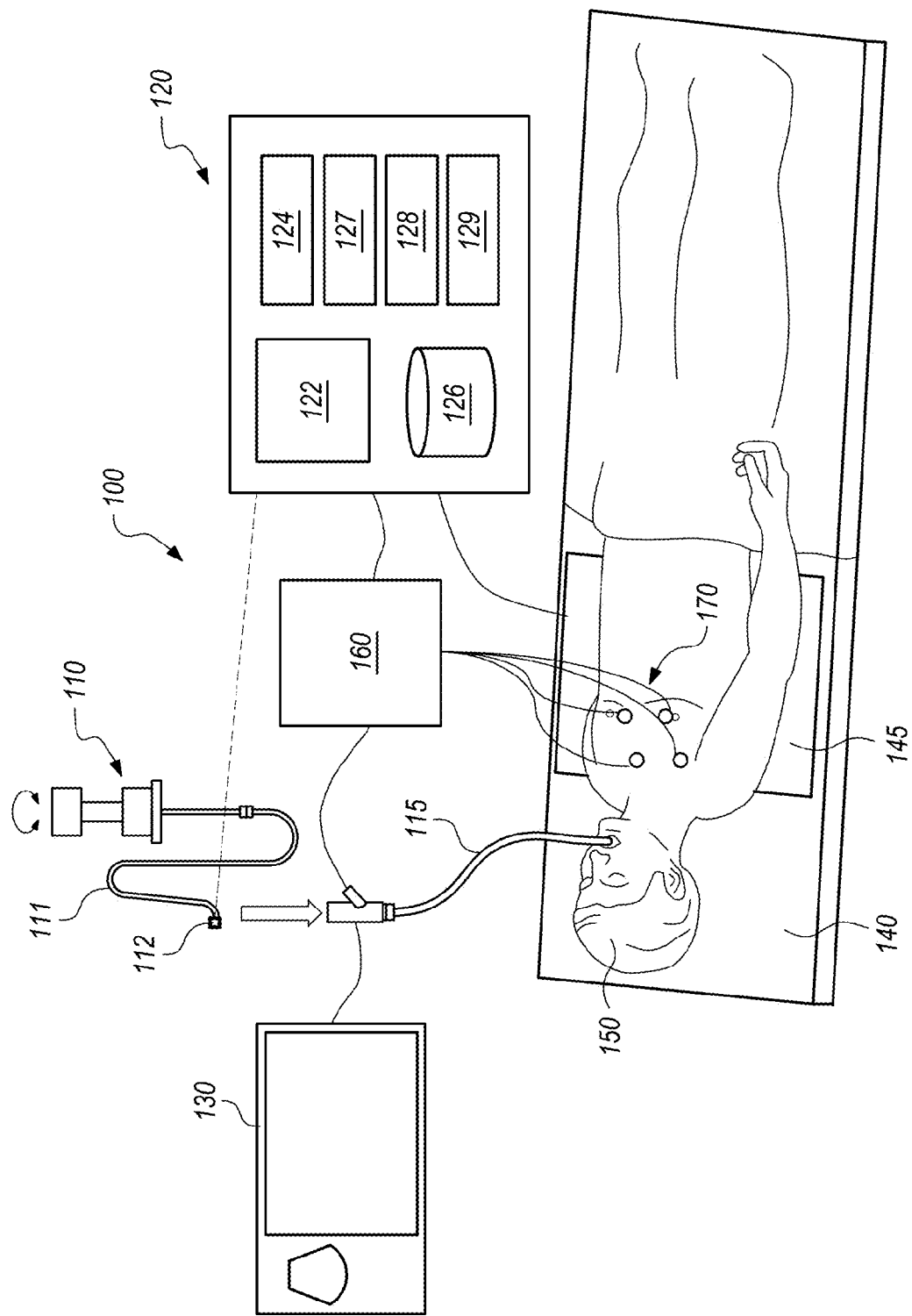
FIG. 1 is a perspective view of an example electromagnetic navigation (EMN) system in accordance with an embodiment of the present disclosure.

The present disclosure is directed to antenna assemblies for radiating electromagnetic fields for electromagnetic navigation, electromagnetic navigation systems that include such antenna assemblies, and computer-implemented methods of designing such antenna assemblies. In one example, by virtue of geometrical and other aspects of an antenna assembly herein, the need to generate and employ a detailed electromagnetic field mapping can be avoided by instead enabling an electromagnetic field mapping, theoretically computed based on characteristics of the antenna assembly, to be employed either alone or in conjunction with a more easily generated low-density electromagnetic field mapping obtained from measurements. In other words, the antenna assembly herein can serve as the basis upon which to generate an accurate high-density theoretical electromagnetic field mapping for EMN, without having to use expensive measuring equipment and without having to perform time-consuming and laborious measurements.

In another example, an antenna assembly herein includes on a single substrate multiple planar antennas having characteristics, such as geometries and/or relative locations that are diverse from one another, that enable multiple (for example, six) degrees of freedom of a small electromagnetic sensor, such as a single-coil sensor, to be determined.

In yet another example, an antenna assembly herein includes a trace that is deposited on a layer of a substrate and that forms multiple loops with the spacing between loops and the spacing from a boundary or edge of the substrate that result in efficient use of the available area of the substrate.

In a further example, an automated, or semi-automated, highly reproducible computer-implemented method for designing an antenna assembly is provided herein. An antenna assembly design generated in this manner can be exported into a printed circuit board (PCB) layout software tool to minimize the need for a large amount of manual layout. The antenna assembly design can also be exported into an electromagnetic field simulator software tool to enable the generation of a theoretical electromagnetic field mapping for the antenna assembly.

Detailed embodiments of antenna assemblies, systems incorporating such antenna assemblies, and methods of designing the same are described herein. These detailed embodiments, however, are merely examples of the disclosure, which may be embodied in various forms. Therefore, specific structural and functional details disclosed herein are not to be interpreted as limiting, but merely as a basis for the claims and as a representative basis for enabling one skilled in the art to variously employ the present disclosure in virtually any appropriately detailed structure. While the example embodiments described below are directed to the bronchoscopy of a patient's airways, those skilled in the art will recognize that the same or similar assemblies, systems, and methods may also be used in other lumen networks, such as, for example, the vascular, lymphatic, and/or gastrointestinal networks.

FIG. 1 illustrates an example electromagnetic navigation (EMN) system 100 provided in accordance with the present disclosure. In general, the EMN system 100 is configured to identify a location and/or an orientation of a medical device being navigated toward a target location within the patient's body by using, among other things, an antenna assembly that generates one or more electromagnetic fields that are sensed by a sensor affixed to the medical device. In some cases, the EMN system 100 is further configured to augment computed tomography (CT) images, magnetic resonance imaging (MRI) images, and/or fluoroscopic images employed during navigation of the medical device through the patient's body toward a target of interest, such as a deceased portion in a luminal network of the patient's lung.

The EMN system 100 includes a catheter guide assembly 110, a bronchoscope 115, a computing device 120, a monitoring device 130, a patient platform 140 (which may be referred to as an EM board), a tracking device 160, and reference sensors 170. The bronchoscope 115 is operatively coupled to the computing device 120 (by way of the tracking device 160) and the monitoring device 130 via respective wired connections (as shown in FIG. 1) or wireless connections (not shown in FIG. 1).

During a navigation phase of an EMN bronchoscopy procedure, the bronchoscope 115 is inserted into the oral cavity of a patient 150 and captures images of the luminal network of the lung. The catheter guide assembly 110 is inserted into the bronchoscope 115 to access the periphery of the luminal network of the lung of the patient 150. The catheter guide assembly 110 may include a catheter or extended working channel (EWC) 111 with an EM sensor 112 affixed to a portion (for example, a distal portion) of the EWC 111. A locatable guide catheter (LG) may be inserted into the EWC 111 with another EM sensor (not shown in FIG. 1) affixed to a portion (for example, a distal portion) of the LG. The EM sensor 112 affixed to the EWC 111 or the EM sensor affixed to the LG is configured to receive a signal based on an electromagnetic field radiated by the antenna assembly 145, and based upon the received signal, is used to determine a location and/or an orientation of the EWC 111 or the LG during navigation through the luminal network of the lung. Due to the size restriction of the EM sensor 112 relative to the EWC 111 or the LG, in some cases the EM sensor 112 may include only a single coil for receiving one or more EM signals generated by way of an antenna assembly 145 as described in further detail below. However, the number of coils in the EM sensor 112 is not limited to one but may be two, three, or more.

The computing device 120, such as a laptop, desktop, tablet, or other suitable computing device, includes a display 122, one or more processors 124, one or more memories 126, an AC current driver 127 for providing AC current signals to the antenna assembly 145, a network interface controller 128, and one or more input devices 129. The particular configuration of the computing device 120 illustrated in FIG. 1 is provided as an example, but other configurations of the components shown in FIG. 1 as being included in the computing device 120 are also contemplated. In particular, in some embodiments, one or more of the components (122, 124, 126, 127, 128, and/or 129) shown in FIG. 1 as being included in the computing device 120 may instead be separate from the computing device 120 and may be coupled to the computing device 120 and/or to any other component(s) of the system 100 by way of one or more respective wired or wireless path(s) to facilitate the transmission of power and/or data signals throughout the system 100. For example, although not shown in FIG. 1, the AC current driver 127 may, in some example aspects, be separate from the computing device 120 and may be coupled to the antenna assembly 145 and/or coupled to one or more components of the computing device 120, such as the processor 124 and the memory 126, by way of one or more corresponding paths.

In some aspects, the EMN system 100 may also include multiple computing devices 120, wherein the multiple computing devices 120 are employed for planning, treatment, visualization, or helping clinicians in a manner suitable for medical operations. The display 122 may be touch-sensitive and/or voice-activated, enabling the display 122 to serve as both an input device and an output device. The display 122 may display two-dimensional (2D) images or three-dimensional (3D) images, such as a 3D model of a lung, to enable a practitioner to locate and identify a portion of the lung that displays symptoms of lung diseases.

The one or more memories 126 store one or more programs and/or computer-executable instructions that, when executed by the one or more processors 124, cause the one or more processors 124 to perform various functions and/or procedures. For example, the processors 124 may calculate a location and/or an orientation of the EM sensor 112 based on the electromagnetic signal that is radiated by the antenna assembly 145 and received by the EM sensor 112. The processors 124 may also perform image-processing functions to cause the 3D model of the lung to be displayed on the display 122. The processors 124 may also generate one or more electromagnetic signals to be radiated by way of the antenna assembly 145. In some embodiments, the computing device 120 may further include a separate graphic accelerator (not shown in FIG. 1) that performs only the image-processing functions so that the one or more processors 124 may be available for other programs. The one or more memories 126 also store data, such as mapping data for EMN, image data, patients' medical record data, prescription data, and/or data regarding a history of the patient's diseases, and/or other types of data.

The mapping data may link multiple grid points, in a coordinate system of an EM volume in which a medical device (e.g., the EWC 111, the LG, treatment probe, or another surgical device) navigates, to the EM signal characteristics (for example, signal strength) that correspond to the grid points, respectively. In this manner, when the EM sensor 112 senses an EM signal having certain characteristics at a particular grid point, the one or more processors 124 may compare the sensed EM signal characteristics to the EM signal characteristics in the mapping data and determine the location and/or orientation of the EM sensor 112 within the EM volume based on a result of the comparison.

As shown in FIG. 1, the platform 140 is configured to provide a flat surface upon which the patient 150 lies during the EMN navigation procedure. The antenna assembly 145, which may also be referred to as an EM field generating device, is arranged upon the platform 140 or is included as a component of the platform 140. The antenna assembly 145 includes one or more antennas, such as planar loop antennas (not shown in FIG. 1). Example aspects of the antenna assembly 145 are described in further detail below.

With the patient 150 lying upon the platform 140, the one or more processors 124 (or another signal generator not shown in FIG. 1) generate and provide to the antenna(s) of the antenna assembly 145 by way of the AC current driver 127 one or more AC current signals that the antenna(s) convert into one or more respective EM signal(s) and radiate in a manner sufficient to surround a portion of the patient 150. In some aspects, the antenna assembly 145 includes a connector that has at least two terminals, and the trace of the antenna (not shown in FIG. 1) has two ends that are coupled to the two connector terminals, respectively, to form a signal communication path from the one or more processors 145 to the antenna.

Figure 2:
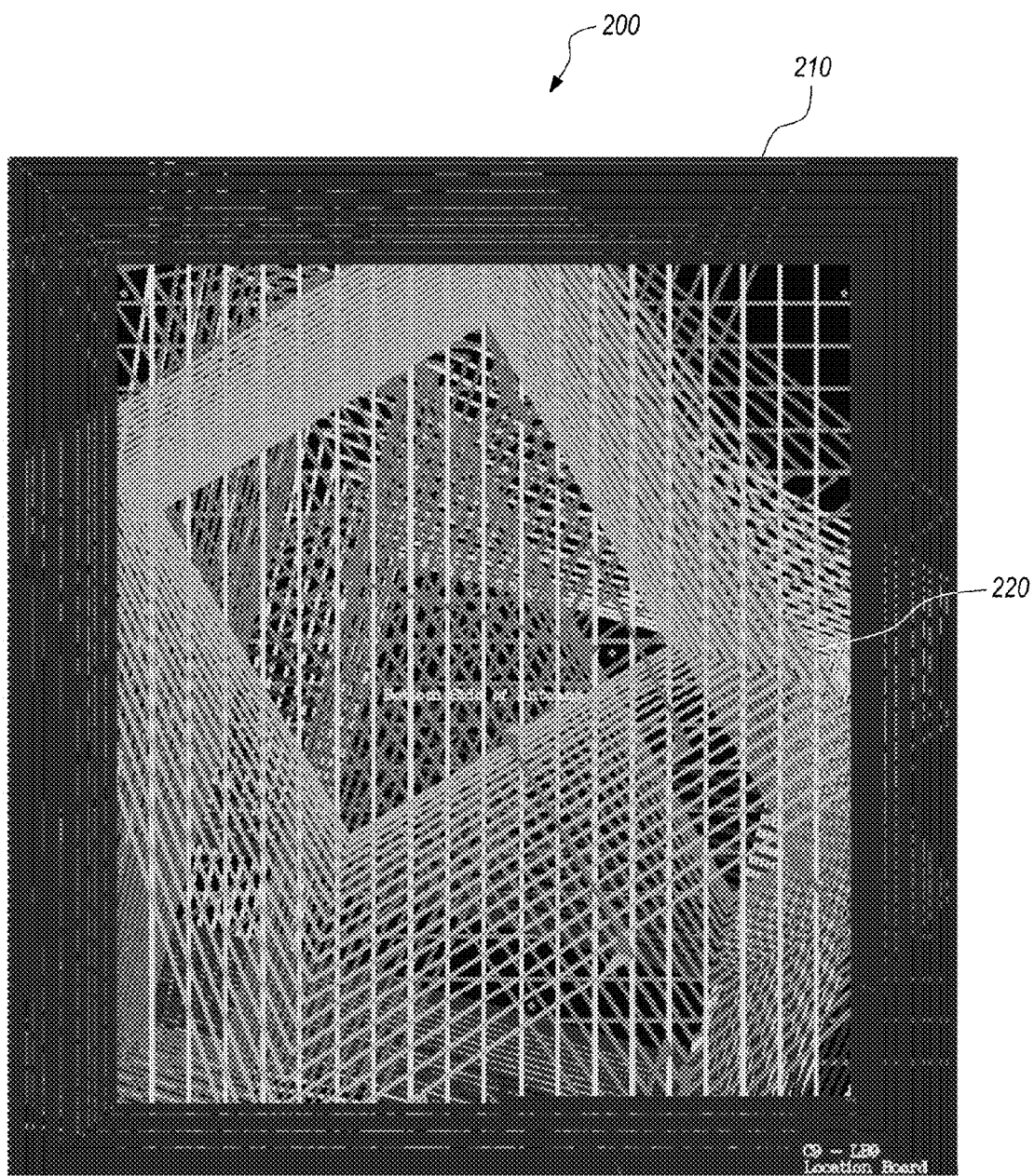
FIG. 2 shows an example design of an antenna assembly of the EMN system in accordance with an embodiment of the present disclosure.

Having described an example EMN system 100, reference will now be made to FIG. 2, which is a graphical illustration of an example antenna assembly layout 200 of the antenna assembly 145 of the EMN system 100, according to an embodiment of the present disclosure. The antenna assembly layout 200 includes a substrate 210, such as a printed circuit board (PCB), which is formed of an electrically insulating material and may include one or more layers. The antenna assembly layout 200 also includes multiple planar antennas 220, which are formed of an electrically conductive material, such as a PCB trace, deposited on the substrate 210 and arranged in multiple loops or as a coil. In one example, each of the planar antennas 220 is deposited on a respective one of the layers of the substrate 210. In the example antenna assembly layout 200 of FIG. 2, multiple layers of the substrate 210 are shown simultaneously.

Each of the multiple antennas may be configured to radiate a separate EM field, for example, using frequency division multiplexing and/or time division multiplexing controlled by the processors 124 or by another generator. For example, the antennas, in some aspects, may be configured to radiate multiple EM fields sufficient in number and/or sufficient in diversity of characteristics (such as frequency, time, modulation scheme, and/or the like) to enable a single-coil electromagnetic sensor mounted on the EWC 111, or on any other medical device, to be used to determine the location and/or the orientation of the sensor, the EWC 111, and/or the medical device. The antenna assembly 145 may, for instance, include six to nine or more loop antennas. In some embodiments, for each of the loop antennas, the distances between its adjacent loops increase as the loops become larger. For example, for each of the planar antennas, respective distances between adjacent pairs of loops may increase in a direction from an innermost one of the loops to an outermost one of the loops of the respective planar antenna. In various embodiments, two or more of the loop antennas of the antenna assembly 145 may have a same number of loops, or may have respectively different numbers of loops.

Having described an example antenna assembly layout 200 of an antenna assembly 145 of the EMN system 100, reference will now be made to FIG. 3, which is a flowchart illustrating an example procedure 300 for designing an antenna assembly such as the antenna assembly 145, in accordance with an embodiment of the present disclosure. In various embodiments, the procedure 300 may be fully computer-implemented or partially computer-implemented. Reference will also be made to FIGS. 4 through 13, which are graphical illustrations of certain steps of the procedure 300, in accordance with an embodiment of the present disclosure. The example method 300 of FIG. 3 may be implemented to design an antenna assembly that includes one antenna or an antenna assembly that includes multiple antennas. For illustrative purposes, the present description of the method 300 will be made in the context of designing an antenna assembly that includes multiple antennas. However, although certain aspects of the method 300 will be described only with respect to the design of a single one of the multiple antennas, those aspects of the method 300 apply similarly to the other ones of the multiple antennas.

Before describing the details of the procedure 300, an overview of the procedure 300 will be provided. In general, according to the procedure 300, the design of the antenna assembly is based on a set of design parameters and/or constraints including a number of antennas M of the antenna assembly to be designed, as well as, for each antenna of the antenna assembly, a seed shape for the antenna, a location of a centroid of the seed shape on the substrate upon which the antenna will be manufactured, a number of loops (N) of the antenna, a minimum trace center-to-center spacing (TCCM) for the antenna, and dimensions of an edge or a boundary of the substrate. Locations of antenna vertices of the antenna are determined based on the seed shape. The antenna design then proceeds by interconnecting the antenna vertices by way of straight linear portions, beginning with the innermost antenna vertices and progressing to the outermost antenna vertices, so that the entire antenna forms a coil including a single trace arranged in multiple loops. In an aspect, each loop of the antenna assembly grows from the seed shape toward the boundaries of the substrate and effectively covers most of the available surface area of the substrate layer outside of the seed shape. The two ends of the trace are routed to a connector location to enable the antenna to be coupled to a signal generator.

For antenna assemblies having multiple planar antennas on respective layers of the multiple layer substrate, this general procedure is repeated for each of the antennas. Additionally, data corresponding to the designed antenna layouts can be exported to an electromagnetic field simulation tool for simulating the electromagnetic field (for example, the theoretical electromagnetic field mapping for EMN described above) that the respective antennas would generate based on their particular characteristics. The data corresponding to the designed antenna layouts can also be exported to a PCB manufacturing tool to enable the antenna assembly to be manufactured in an automated manner, in accordance with the designed antenna layouts.

Figure 4:
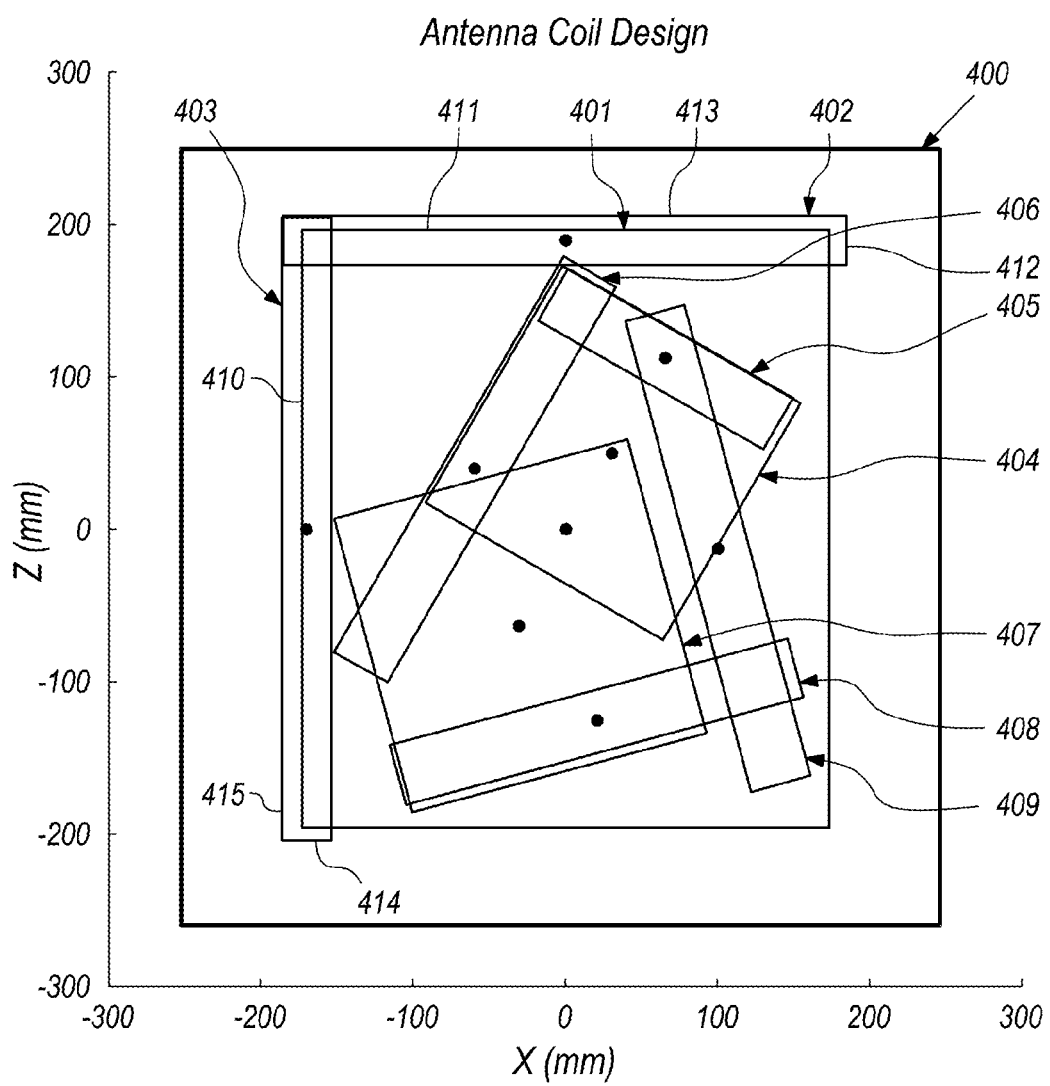
FIGS. 4-11 are example graphical representations of certain aspects of the procedure of FIG. 3, in accordance with an embodiment of the present disclosure.

Before describing the details of the procedure 300, reference will be made to FIG. 4 to describe example seed shapes and their characteristics. In particular, FIG. 4 shows examples of nine seed rectangles 401 through 409 of an antenna assembly to be designed according to the procedure 300. Each of the seed rectangles 401 through 409 includes four vertices within the edge 400 of the substrate. The number of seed rectangles, and hence the number of antennas M, shown in the example of FIG. 4 is nine, however, this is for illustrative purposes only and should not be construed as limiting. In other embodiments, the number of seed shapes, and hence the number of antennas M, may be, for example, six, nine, or more. As an example, the square 400 may represent the edge of the substrate, and a boundary (not shown in FIG. 4) that represents the area of the substrate that is available for placement of the antennas may be formed from a square within the x-z plane that is contained within the edge 400 of the substrate and smaller than the edge 400 of the substrate by some predetermined threshold or buffer amount.

In another example, an antenna assembly herein includes on a single substrate (for example, on respective layers of a multiple-layer substrate) multiple planar antennas having characteristics, such as geometries and/or relative locations that are diverse from one another, that enable multiple (for example, six) degrees of freedom of a small electromagnetic sensor, such as a single-coil sensor, to be determined. For instance, as shown in FIG. 4, the nine seed rectangles 401-409 may be grouped in three, with seed rectangles 401-403 being in a first group; seed rectangles 404-406 being in a second group; and seed rectangles 407-409 being in a third group. As shown in FIG. 4, the three seed rectangles in each group have specific geographical relationships with respect to one another. For instance, one seed rectangle is a square (or substantially square-like), and the other two seed rectangles are non-square rectangles and are located near two sides of the square. For example, the seed rectangle 401 is a square, the seed rectangle 402 is located in line with the length of the seed rectangle 401, and the seed rectangle 403 is located in line with the width of the seed rectangle 401. Further, the length of the seed rectangle 402 is longer than the width of the square 401, and is similar to the length of the seed rectangle 401, while the width of the seed rectangle 402 is smaller than the width of the square 401; and the width of the seed rectangle 403 is longer than the length of the square 401 and is similar to the width of the square 401, while the length of the seed rectangle 402 is smaller than the length of the square 401. The seed rectangles 404-406 of the second group and the seed rectangles 407-409 of the third groups also have the similar geometric features as the seed rectangles 401-403 of the first group.

Put differently, for each of multiple groups of planar antennas that may be generated based on the seed rectangles 401-409: an innermost loop of the first planar antenna (for example, corresponding to the seed rectangle 401) has a first linear portion (for example, first linear portion 410) and a second linear portion (for example, second linear portion 411) approximately perpendicular to the first linear portion (for example, first linear portion 410); an innermost loop of the second planar antenna (for example, corresponding to the seed rectangle 402) has a first linear portion (for example, first linear portion 412) and a second linear portion (for example, second linear portion 413) approximately perpendicular to, and longer than, the first linear portion (for example, first linear portion 412); an innermost loop of the third planar antenna (for example, corresponding to the seed rectangle 403) has a first linear portion (for example, first linear portion 414) and a second linear portion (for example, second linear portion 415) approximately perpendicular to, and longer than, the first linear portion (for example first linear portion 414); the first linear portion (for example, first linear portion 412) of the seed rectangle of the innermost loop of the second planar antenna is approximately parallel to the first linear portion (for example, first linear portion 410) of the innermost loop of the first planar antenna; and the first linear portion (for example, first linear portion 414) of the innermost loop of the third planar antenna is approximately parallel to the second linear portion (for example, second linear portion 411) of the innermost loop of the first planar antenna. Although additional reference numbers for the first and second linear portions of the seed rectangles 404-409 (and hence the correspondence planar antennas) are omitted from FIG. 4 for clarity, the seed rectangles 404-406 of the second group and the seed rectangles 407-409 of the third groups each have similar geometric relationships with respect to one another, as those described above in the context of the seed rectangles 401-403 of the first group.

In an aspect, these three groups may be geometrically dispersed from each group within the substrate 210. Dispersion may be accomplished by geometric relationship and/or angular relationship. For example, the respective innermost loops of the planar antennas of each group can be positioned, on the respective layers of the multiple-layer substrate, at respective angles that are distinct from one another. Additionally, the planar antennas, and/or the seed rectangles upon which the planar antennas are based, may have respective centroids (for example represented by circular dots in FIG. 4), relative to a plane of the substrate, that are mutually distinct from one another. Further, the outer boundaries of the first group include all seed rectangles 404-409 of the second and third groups. Also, the seed rectangles 404-409 of the second and third groups are geometrically dispersed within the outer boundaries of the first group.

Further, each group has an angular relationship with respect to the two axes (i.e., the x axis and the z axis). For example, the seed rectangle 401 of the first group is congruent with the two axes, while the seed rectangles 404 and 407 of the second and third groups are angled with respect to the two axes with different angles, respectively. In other words, the smallest angle between the seed rectangle 401 or the square of the first group and the x axis is zero; the smallest angle between the seed rectangle 404 and the x axis is greater than zero but less than the smallest angle between the seed rectangle 407 of the third group and the x axis. However, the relationship among three groups is not limited to the geometric and angular relationships but can be expanded in any readily conceivable way for a person having ordinary skill in the art within the scope of this disclosure.

Four vertices of each of the seed rectangles 401-409 may be provided in a coordinate form (x, z) in the x-z plane. In an aspect, a centroid of each of the seed rectangles 401-409 may also be provided in coordinate form or can be calculated from the four vertices. Dispersion may also be achieved by dispersing the centroids within the substrate 210. In an aspect, centroids of all seed rectangles 401-409 are disposed on the substrate in positions that are distinct from each other.

Figure 3:
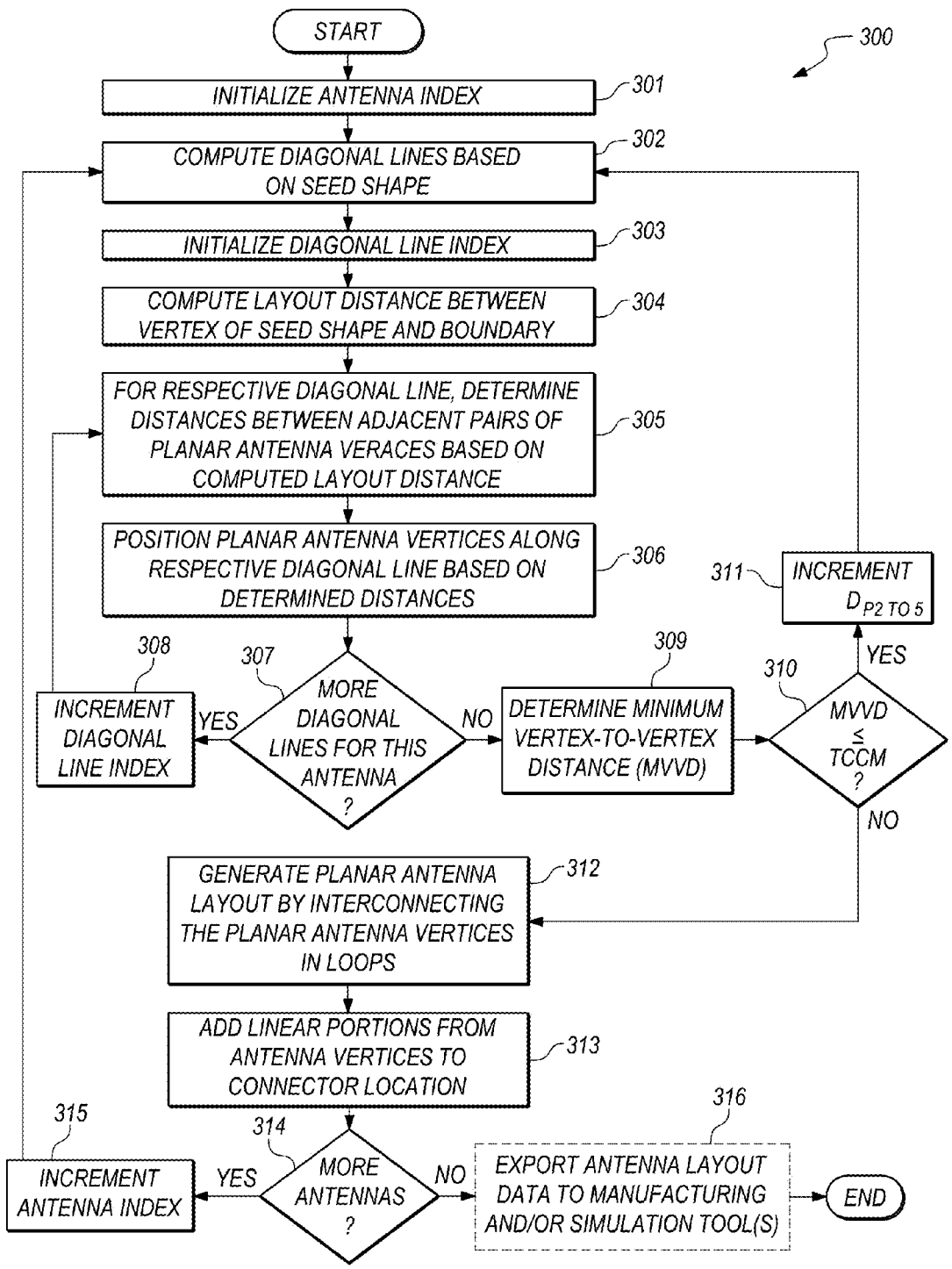
FIG. 3 is a flowchart illustrating an example procedure for designing an antenna assembly in accordance with an embodiment of the present disclosure.

Referring now to FIG. 3, prior to block 301, a set of design parameters and/or constraints for the first antenna of the antenna assembly to be designed (for example, a seed shape for the antenna, a location of a centroid of the seed shape on a substrate upon which the antenna will be manufactured, a number of loops (N) of the antenna, a minimum trace center-to-center spacing (TCCM) for the antenna, and dimensions of an edge or a boundary of the substrate) are set (not shown in FIG. 3). For illustrative purposes, the seed shapes utilized in the procedure 300 for each antenna are seed rectangles; however, this should not be construed as limiting. Other seed shapes (for example, a seed triangle, a seed pentagon, a seed hexagon, any convex polygon, convex curved shape (e.g., an ellipse, an egg, a circle, etc.), or any other suitable seed shape) are contemplated and can be employed in the procedure 300. In some embodiments, any combination of different seed shapes can be used for the antennas of the antenna assembly, respectively. Each seed shape has multiple vertices. More specifically, each seed rectangle has four vertices.

At block 301, an antenna index $i_{antenna}$ is initialized. For example, $i_{antenna}$ is set equal to 1 to correspond to the first antenna of the multiple (M, where M>1) antennas of the antenna assembly to be designed. As described below, the purpose of the antenna index $i_{antenna}$ is to enable the procedure 300 to be repeated, in the case of antenna assemblies including multiple antennas, for each antenna of the M antennas of the antenna assembly. For instance, in some examples, the substrate has multiple layers (for example, as in a multi-layer PCB) and the method 300 is employed to generate multiple planar antenna layouts corresponding to the antennas to be deposited on corresponding ones of the multiple layers of the substrate.

At block 302, multiple diagonal lines are computed, relative to a coordinate system of the substrate, based on the seed rectangle. In general, the number of diagonal lines computed at block 302 equals the number of vertices of the seed shape. In particular, in the case of the seed rectangle, which has four vertices, four diagonal lines are computed that bisect the four vertices of the seed rectangle, respectively, and extend from the four vertices of the seed rectangle, respectively, to the boundary of the substrate. The boundary of the substrate may be a physical boundary of the substrate, such as an edge of a PCB, or may be a theoretically imposed boundary, such as a boundary offset from the edge of the PCB by a predetermined buffer distance.

Figure 5:
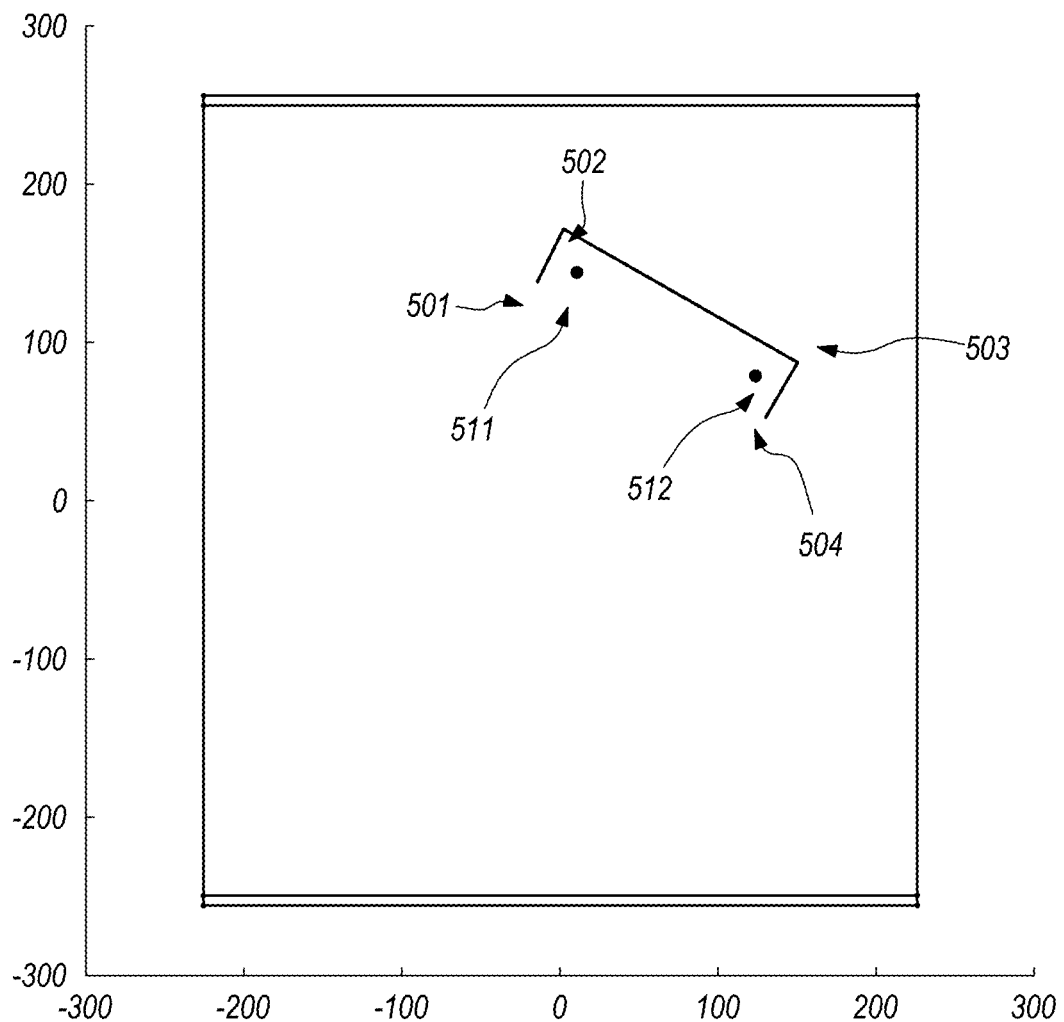

In one example, as part of the computing of the multiple diagonal lines performed at block 302, origins for the diagonal lines of each of vertex of the seed rectangle are first calculated, and then vertices of the innermost loop of the antenna (also referred to as seed vertices) are determined based on the seed rectangle. For example, FIG. 5 shows origins 511 and 512 that are calculated for the seed rectangle 405 of FIG. 4. The origins 511 and 512 are bounded by the four vertices 501 through 504 of the seed rectangle 405. In an aspect, one origin may correspond to a single vertex of the seed rectangle, or one origin may correspond to two adjacent vertices. In another aspect, the origins 511 and 512 may be located on the diagonals of the seed rectangle or on the diagonals which bisect the corresponding angle to form two 45 degree angles. In this case, diagonals define the locations of vertices of the loop antenna. As an example, the origin 511 is located on a diagonal, which bisects the 90 degree angle at the vertex 501 to form two 45 degree angles. Also as shown in FIG. 5, the origin 511 is located on the intersection of the diagonals which bisect the angles at vertices 501 and 502. In the same way, the origin 512 is located at the intersection of the diagonals which bisect the angles at vertices 503 and 504. In one example, the origins for the diagonal lines of each vertex of the seed rectangle can be calculated by performing principal component analysis (PCA) over the coordinates of the four vertices 501-504, utilizing singular value decomposition. The following notations are used herein:

$P_{jk}$ represents the k-th vertex of the j-th loop, where j is 1 to N and k is 1 to 4;

$P_{jkx}$ and $P_{jkz}$ represent x-coordinate and z-coordinate of the vertex $P_{jk}$, respectively;

$\{P_{j1}, P_{j2}, P_{j3}, P_{j4}\}$ or simply $\{P_{jk}\}$ is a 4 by 2 matrix having four vertices $P_{j1}, P_{j2}, P_{j3}, P_{j4}$ of the j-th loop as its rows;

U represents a 4 by 4 matrix having orthonormal eigenvectors of $\{P_{jk}\}\{P_{jk}\}^T$ as its column;

V represents a 2 by 2 matrix having orthonormal eigenvectors of $\{P_{jk}\}^T\{P_{jk}\}$ as its column; and S represents a 4 by 2 matrix, whose nonzero elements are located only at its diagonal and are square root of eigenvalues of $\{P_{jk}\}\{P_{jk}\}^T$ or $\{P_{jk}\}^T\{P_{jk}\}$; and $\tilde{S}$ represents a 4 by 2 matrix, whose nonzero elements are located only at its diagonal and are equal to the smallest nonzero element of S.

Given the four vertices $R_k$, $(R_{kx}, R_{kz})$, of the i-th seed rectangle, a centroid C, $(C_x, C_z)$, of the i-th seed rectangle is calculated as follows:

$$(C_x, C_z) = \left(\frac{\sum_{k=1}^{4} R_{kx}}{4}, \frac{\sum_{k=1}^{4} R_{kz}}{4}\right). \quad (1)$$

By performing singular value decomposition on the centroid-subtracted four vertices $R_j$, S, V, and D matrices are obtained as follows:

$$USV^T = \{R_k - C\} \quad (2),$$

where $\{R_k - C\}$ is a 4 by 2 matrix, each row of $\{R_k - C\}$ is the centroid-subtracted vertex $(R_{kx} - C_x, R_{kz} - C_z)$, and k is 1 to 4.

S is a 4 by 2 matrix having nonzero elements only in the diagonal, i.e., $S_{11}$ and $S_{22}$. Based on the singular value decomposition, $S_{11}$ is greater than or equal to $S_{22}$. By replacing the value of $S_{11}$ with the value of $S_{22}$, we can get a new 4 by 2 diagonal matrix $\tilde{S}$, where $\tilde{S}_{11}$ and $\tilde{S}_{22}$, are equal to $S_{22}$. Then, the origins $O_k$ for each vertex can be obtained by the following:

$$\{O_k\} = \{R_k\} - U\tilde{S}V^T \quad (3).$$

Because the diagonal entries of $\tilde{S}$ are the minimum values of the diagonal entries of S, $\{O_k\}$ includes only two different rows, corresponding to the origins 511 and 512, within the i-th seed rectangle, as shown in FIG. 5.

After obtaining the origins 511 and 512, a first set of four seed vertices $P_{1k}$ within the i-th seed rectangle are determined. These first four seed vertices $P_{1k}$ are the seed vertices for the innermost loop of the respective antenna and can be used to determine the other vertices of that antenna.

Figure 6:
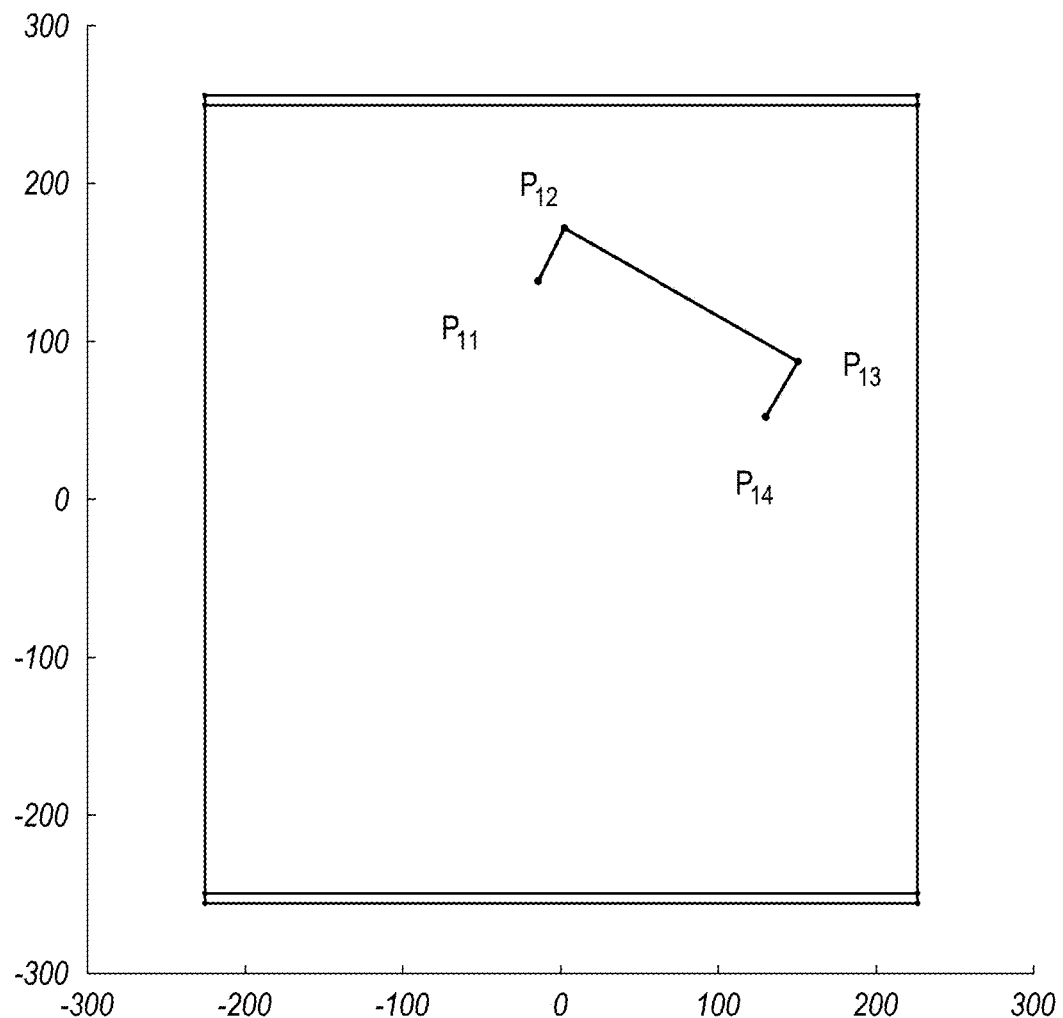
Figure 7:
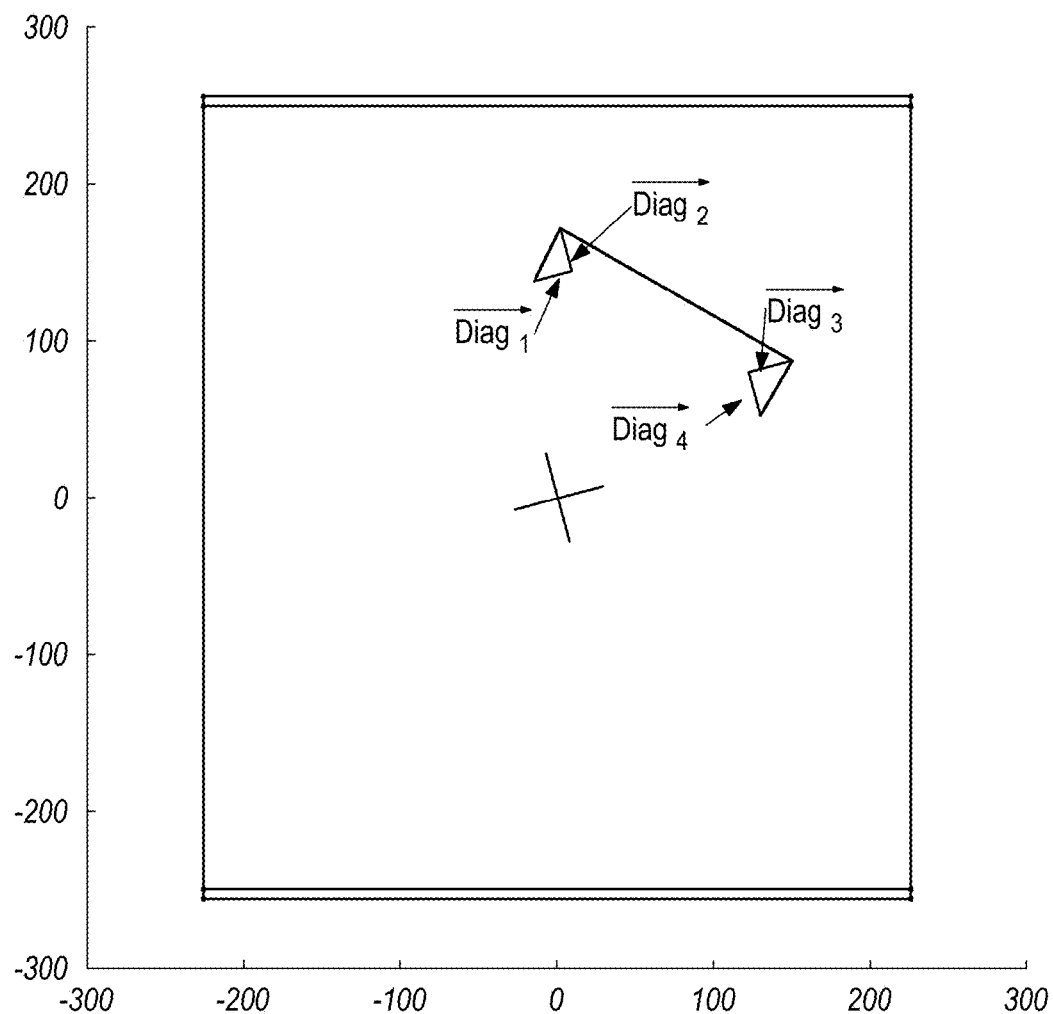

Given the minimum trace center-to-center (TCCM) spacing, which represents a predetermined minimum distance between traces or loops of a particular antenna or of all the antennas of a particular antenna assembly, the first seed vertex $P_{11}$ is determined by moving $R_1$ into its corresponding diagonal, which bisects the 90 degree angle at $R_1$, toward the inside of the i-th seed rectangle. This can be done by first defining two vectors from $R_1$ as follows:

$$\vec{V}_{R_{14}} = \vec{R}_4 - \vec{R}_1 \quad (4),$$

$$\vec{V}_{R_{12}} = \vec{R}_2 - \vec{R}_1 \quad (5),$$

where $\vec{R}_k$ is a vector pointing toward $R_k$ from the respective origin $O_k$, $\vec{V}_{R_{14}}$ is a vector pointing toward $R_4$ from $R_1$, and $\vec{V}_{R_{12}}$ is a vector pointing toward $R_2$ from $R_1$. By adding the unit vector of $$\vec{V}_{R_{14}}, \frac{\vec{V}_{R_{14}}}{\|\vec{V}_{R_{14}}\|},$$

to the unit vector of $$\vec{V}_{R_{12}}, \frac{\vec{V}_{R_{12}}}{\|\vec{V}_{R_{12}}\|},$$

a vector having a direction in line with the respective diagonal line, which bisects the 90 degree angle at $R_1$ to form two 45 degree angles, is obtained, where the symbol "$\|\|$" represents a magnitude of the vector inside of the symbol "$\|\|$". Then, the first seed vertex $P_{11}$ is obtained by the following equation:

$$\vec{P}_{11} = \vec{R}_1 + TCCM \times \left(\frac{\vec{V}_{R_{14}}}{\|\vec{V}_{R_{14}}\|} + \frac{\vec{V}_{R_{12}}}{\|\vec{V}_{R_{12}}\|}\right), \quad (6)$$

where $\vec{P}_{11}$ is a vector originating from the respective origin $O_1$ and thus represents a coordinate of $P_{11}$. FIG. 6 illustrates the other three seed vertices $P_{12}$, $P_{13}$, and $P_{14}$ of the antenna, which match $R_2$, $R_3$, and $R_4$. The smallest distance between $P_{1k}$ and the four sides of the i-th seed rectangle equals TCCM. FIG. 7 shows vectors $Diag_1$, $Diag_2$, $Diag_3$, and $Diag_4$, which may form respective portions of the diagonal lines that bisect the seed vertices $P_{11}$, $P_{12}$, $P_{13}$, and $P_{14}$ and extend from the respective seed vertices $P_{11}$, $P_{12}$, $P_{13}$, and $P_{14}$ to the boundary of the substrate.

Referring back to FIG. 3, at block 303 a diagonal line index $i_{diagonal}$ is initialized. For example, $i_{diagonal}$ is set equal to 1 to correspond to the first diagonal line of the four diagonal lines of the seed rectangle. As described below, the purpose of the diagonal line index $i_{diagonal}$ is to enable aspects of the procedure to be repeated for each of the diagonal lines of the seed rectangle.

At block 304, for the respective diagonal line, a vertex-layout-distance (also referred to herein as a layout distance) $V_{layout\_k}$ between the respective vertex of the seed rectangle and the boundary of the substrate, along the respective diagonal line is computed. The layout distance may represent, or may be related to, the maximum usable distance between the respective vertex of the seed rectangle and the boundary of the substrate.

Figure 9:
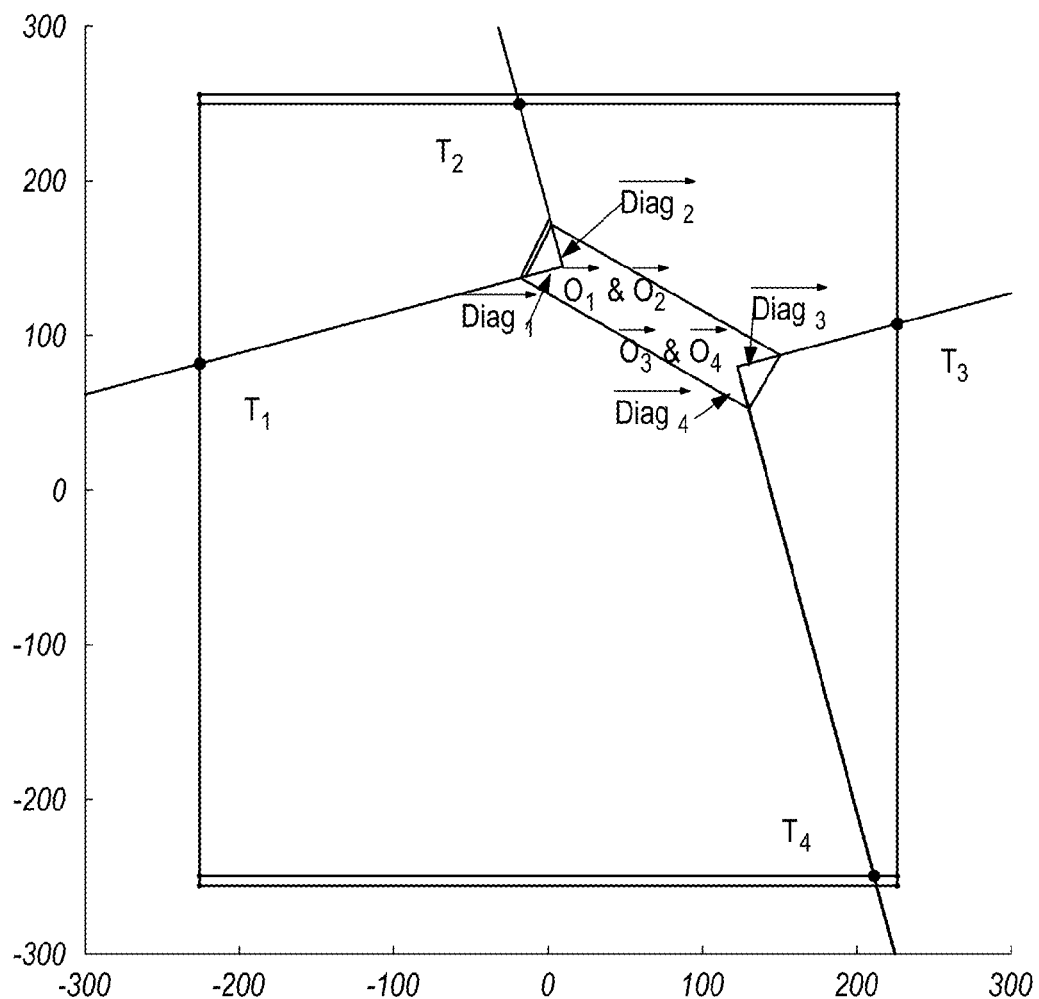

In some example embodiments, as part of the computing of the layout distance at block 304, respective intersecting points $T_k$ between the origins $O_k$ and the boundary of the substrate, when the respective diagonals $\overrightarrow{Diag_k}$ are projected from the origins $O_k$, are calculated and identified, as shown, for example, in FIG. 9. The intersecting points $T_k$ can be found using multiple conventional approaches. When the intersecting points $T_k$ are found, the following relationship is satisfied:

$$\frac{\overrightarrow{O_k T_k}}{\|\overrightarrow{O_k T_k}\|} = \frac{\overrightarrow{Diag_k}}{\|\overrightarrow{Diag_k}\|}, \tag{14}$$

where $\overrightarrow{O_k T_k}$ is a vector from the origin $O_k$ to the intersecting point $T_k$. In other words, vector $\overrightarrow{O_k T_k}$ has the same direction as the diagonal vector $\overrightarrow{Diag_k}$.

With the four vertices $P_{11}$, $P_{12}$, $P_{13}$, and $P_{14}$ of the first loop and the intersecting points $T_1$, $T_2$, $T_3$, and $T_4$ identified, the vertex-layout-distance, $V_{layout\_k}$, can be calculated from the following equation:

$$V_{layout\_k} = \|\overrightarrow{P_{1k} T_k}\| - \frac{VVM}{2}. \tag{15}$$

The subtracting term, $$\frac{VVM}{2},$$

ensures that the last vertex $P_{Nk}$ of the N-th loop is distant from the intersecting point $T_k$. In other words, only a $V_{layout\_k}$-long linear portion starting from $P_{1k}$ is used to distribute (N–1) vertices between $P_{1k}$ and $T_k$.

After the intersecting points $T_k$ are identified, every vertex for the loop antenna can be determined. As one of the initial conditions is that the number of loops of the loop antenna is N and the four vertices $P_{11}$, $P_{12}$, $P_{13}$, and $P_{14}$ of the first loop are determined in step 330, four vertices of each of the second, third, . . . , and N-th loops are recursively determined. In particular, at block 305, for the respective diagonal line, respective distances between adjacent pairs of planar antenna vertices to be positioned along the respective diagonal line are determined based at least in part on the layout distance computed at block 304. For example, the respective distances between adjacent pairs of planar antenna vertices to be positioned along the respective diagonal line may be determined so as to fit the predetermined number of loops N of the antenna while maximizing the use of the available linear distance from the vertex of the seed rectangle to the boundary of the substrate. In this manner, the available area of the substrate may be efficiently utilized. Additionally, in some example aspects, an outermost planar antenna vertex of the planar antenna vertices of the respective planar antenna is distanced from the boundary of the substrate by not more than a predetermined threshold, for efficient utilization of the available substrate area.

Figure 10:
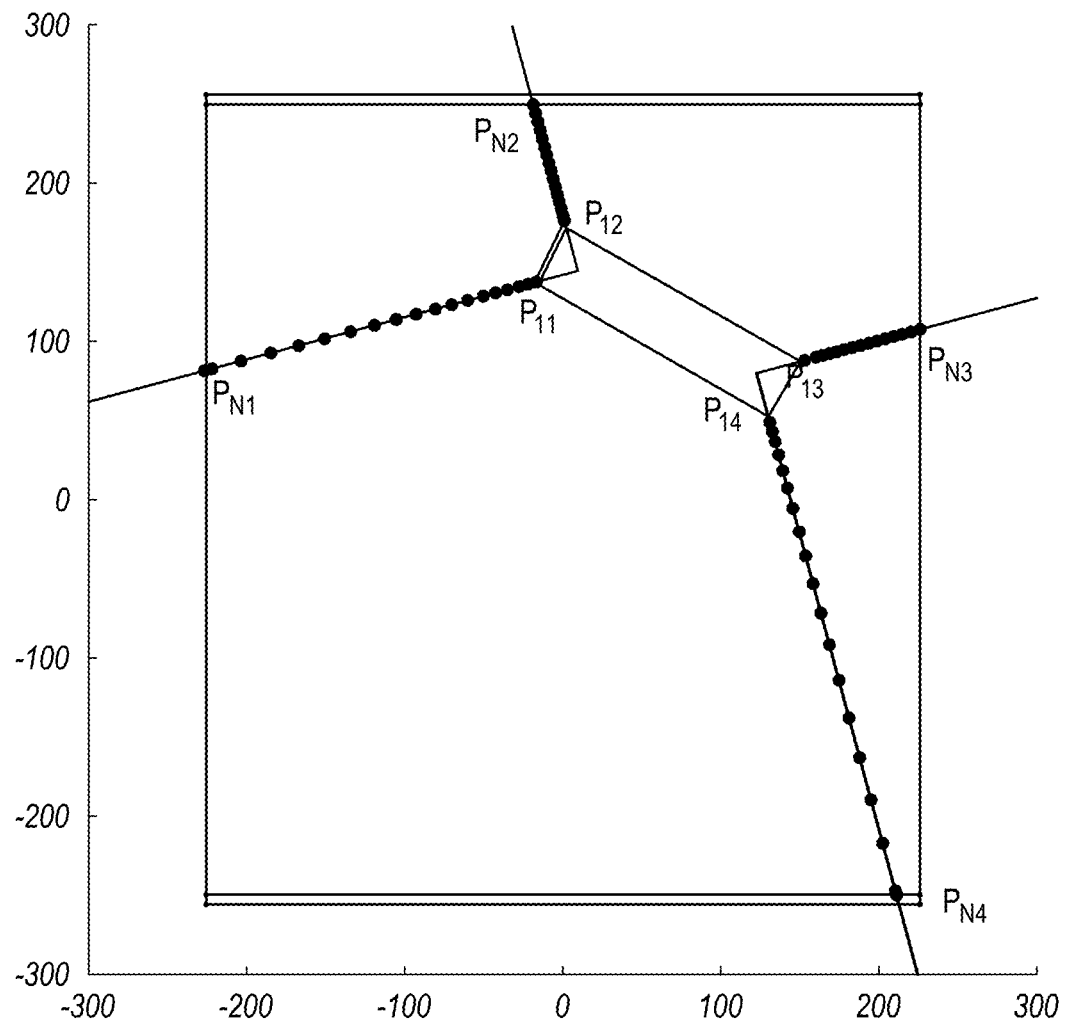

In some examples, the respective distances are determined at block 305 based at least in part on the predetermined number N of loops of the planar antenna, a predetermined minimum spacing between adjacent vertices, a predetermined minimum spacing between adjacent traces, and/or any combination of one or more of those factors or other factors. In particular, in one example, vertices are grouped in four groups with each group forming a rectangular shape, and vertices in the same group are described as corresponding vertices. For example, the first group includes $P_{11}$, $P_{21}$, . . . , and $P_{N1}$, the second group includes $P_{12}$, $P_{22}$, . . . , and $P_{N2}$, the third group includes $P_{13}$, $P_{23}$, . . . , and $P_{N3}$, and the fourth group includes $P_{14}$, $P_{24}$, . . . , and $P_{N4}$. Thus, $P_{3k}$ and $P_{Nk}$ are in the same k-th group and are corresponding vertices, while $P_{33}$ and $P_{42}$ are not in the same group and cannot be corresponding vertices. For each group, the distance between $P_{jk}$ and $P_{(j+1)k}$ is set to be greater than the distance between $P_{(j-1)k}$ and $P_{jk}$, where j is 2 to N–1 and k is 1 to 4. In other words, the distance between two adjacent corresponding vertices is increasing toward the boundary of the substrate. Put differently, in one example, as illustrated in FIG. 10, the distances between the adjacent pairs of antenna vertices become progressively larger in a direction from an innermost one of the vertices to an outermost one of the vertices. The progressively increasing distance in a direction from the respective vertex of the seed rectangle to the boundary may be implemented by various methods, such as arithmetic progression, geometric progression, exponential progression, and/or the like.

For example, arithmetic progression may be employed to distribute remaining vertices in each group. Letting $d_{jk}$ be the distance between $P_{jk}$ and $P_{(j+1)k}$ in the k-th group and be expressed in recursive form as:

$$\|\overrightarrow{P_{jk} P_{(j+1)k}}\| = d_{jk} \tag{16},$$

$$d_{jk} = slope_k \times (j-1) + d_{1k} \tag{17, and}$$

$$d_{1k} = VVM \tag{18},$$

where $\|\overrightarrow{P_{jk} P_{(j+1)k}}\|$ represents a distance between vertices $P_{jk}$ and $P_{(j+1)k}$, $slope_k$ is a constant for the k-th group, which is the common difference between two distances $d_{jk}$ and $d_{(j+1)k}$, and j is 1 to (N–2). Thus, each vertex in the k-th group is positioned on the linear portion connecting $T_k$ and $P_{1k}$ and the total length between $P_{Nk}$ and $P_{1k}$ is less than or equal to the vertex-layout-distance, $V_{layout\_k}$. In order to make an additional keepout area of half the minimum trace center to center (TCCM) spacing between the $T_k$ and $P_{Nk}$, the following equation may be satisfied:

$$\sum_{j=1}^{N-1} \|\overrightarrow{P_{jk} P_{(j+1)k}}\| = V_{layout\_k} - \frac{TCCM}{2}, \tag{19}$$

or $$\sum_{j=1}^{N-1} d_{jk} = \sum_{j=1}^{N-1} (slope_k \times (j-1) + d_{1k}) = V_{layout\_k} - \frac{TCCM}{2}. \tag{20}$$

When equation (20) is solved for the constant, slope$_k$, the following equation can be obtained:

$$slope_k = \frac{2 \cdot \left(V_{layout\_k} - (N-1)d_{1k} - \frac{TCCM}{2}\right)}{(N-1)(N-2)}. \quad (21)$$

When the equation (20) is combined with equations (16) and (17), the following equation is obtained:

$$\|\overrightarrow{P_{jk}P_{(j+1)k}}\| = \frac{2 \cdot \left(V_{layout\_k} - (N-1)d_{1k} - \frac{TCCM}{2}\right)}{(N-1)(N-2)}(j-1) + d_{1k}. \quad (22)$$

In this way, the distance between two adjacent corresponding vertices $P_{jk}$ and $P_{(j+1)\ k}$ increases as j increases. This progressive pattern between corresponding vertices is shown in FIG. 10 more clearly in the first and the fourth groups than in the second and the third groups.

At block 306, the planar antenna vertices are positioned along the respective diagonal line based on the respective distances between adjacent pairs of planar antenna vertices determined at block 305.

At block 307, the diagonal line index $i_{diagonal}$ is compared to the number of diagonal lines, namely four, of the seed rectangle to determine whether the procedures of block 305 and block 306 are to be repeated for additional diagonal lines of the respective antenna. If it is determined at block 307 that $i_{diagonal}$ is less than the number of diagonal lines, then at block 308 $i_{diagonal}$ is incremented by one to correspond to the next diagonal line (for example, the second diagonal line) of the four diagonal lines of the seed rectangle. Then the procedures of block 305 and block 306 are repeated for that next diagonal line in the manner described above.

If, on the other hand, it is determined at block 307 that $i_{diagonal}$ is equal to the number of diagonal lines, indicating that the procedures of block 305 and block 306 have been executed for each of the four diagonal lines of the seed rectangle, then at block 309, a minimum vertex to vertex distance (VVM) is calculated to make sure that, when vertices are connected by linear portions or segments of a line, the smallest distance between two adjacent corresponding linear portions is greater than TCCM, where the phrase "two adjacent corresponding linear portions" being used to refer to linear portions that are positioned in different loops but are located closer to one another than any other linear portions. This is done by defining diagonal vectors $\overrightarrow{Diag_k}$, setting up temporary vertices P'$_{21}$ and P'$_{22}$, measuring a distance between a linear portion connecting the temporary vertices P'$_{21}$ and P'$_{22}$ and a linear portion connecting P$_{11}$ and P$_{12}$, and adjusting a value of VVM until the smallest distance is greater than TCCM. Details of this step are further described below.

The diagonal vectors $\overrightarrow{Diag_k}$ are defined as follows:

$$\overrightarrow{Diag_k} = \overrightarrow{P_{1k}} - \overrightarrow{O_k} \quad (7)$$

where k is 1 to 4. When these diagonal vectors $\overrightarrow{Diag_k}$ are arranged at the origin (0, 0), they form a cross indicating that they form four 90 degree angles as shown in the middle of FIG. 7.

A temporary distance D$_{p2to5}$ is initialized as the value of TCCM. Vectors $\overrightarrow{V_{P_{32}}}$, $\overrightarrow{P'_{22temp}}$, and $\overrightarrow{V_{P_{22temp}}}$ are defined by the following:

$$\overrightarrow{V_{P_{32}}} = \overrightarrow{P_{12}} - \overrightarrow{P_{13}}, \quad (8)$$

$$\overrightarrow{P'_{22temp}} = \overrightarrow{P_{12}} + D_{p2to5} \times \frac{\overrightarrow{V_{P_{32}}}}{\|\overrightarrow{V_{P_{32}}}\|}, \quad (9)$$

and $$\overrightarrow{V_{P_{22temp}}} = \overrightarrow{P'_{22temp}} - \overrightarrow{P_{12}}. \quad (10)$$

Temporary vertex P'$_{22}$ is defined in a vector form as follows:

$$\overrightarrow{P'_{22}} = \overrightarrow{P_{12}} + \frac{\overrightarrow{Diag_2}}{\|\overrightarrow{Diag_2}\|} \times \frac{\|\overrightarrow{V_{P_{22temp}}}\|^2}{\overrightarrow{V_{P_{22temp}}} \cdot \frac{\overrightarrow{Diag_2}}{\|\overrightarrow{Diag_2}\|}}, \quad (11)$$

where the symbol "." is a dot product between two vectors. In short, temporary vertex P'$_{22}$ is distant from P$_{12}$ by $\sqrt{2} \times$TCCM in a direction of the diagonal $\overrightarrow{Diag_2}$ toward outside of the i-th seed rectangle. Next, VVM is temporarily initialized with the following equation:

$$VVM = \|\overrightarrow{P'_{22}} - \overrightarrow{P_{12}}\| \quad (12).$$

Temporary vertex P'$_{21}$ is defined in a vector form as follows:

$$\overrightarrow{P'_{21}} = \overrightarrow{P_{11}} + VVM \times \frac{\overrightarrow{Diag_1}}{\|\overrightarrow{Diag_1}\|}. \quad (13)$$

As with P'$_{22}$, temporary vertex P'$_{21}$ is distant from P$_{11}$ by $\sqrt{2} \times$TCCM in a direction of the diagonal $\overrightarrow{Diag_1}$ toward outside of the i-th seed rectangle.

Figure 8:
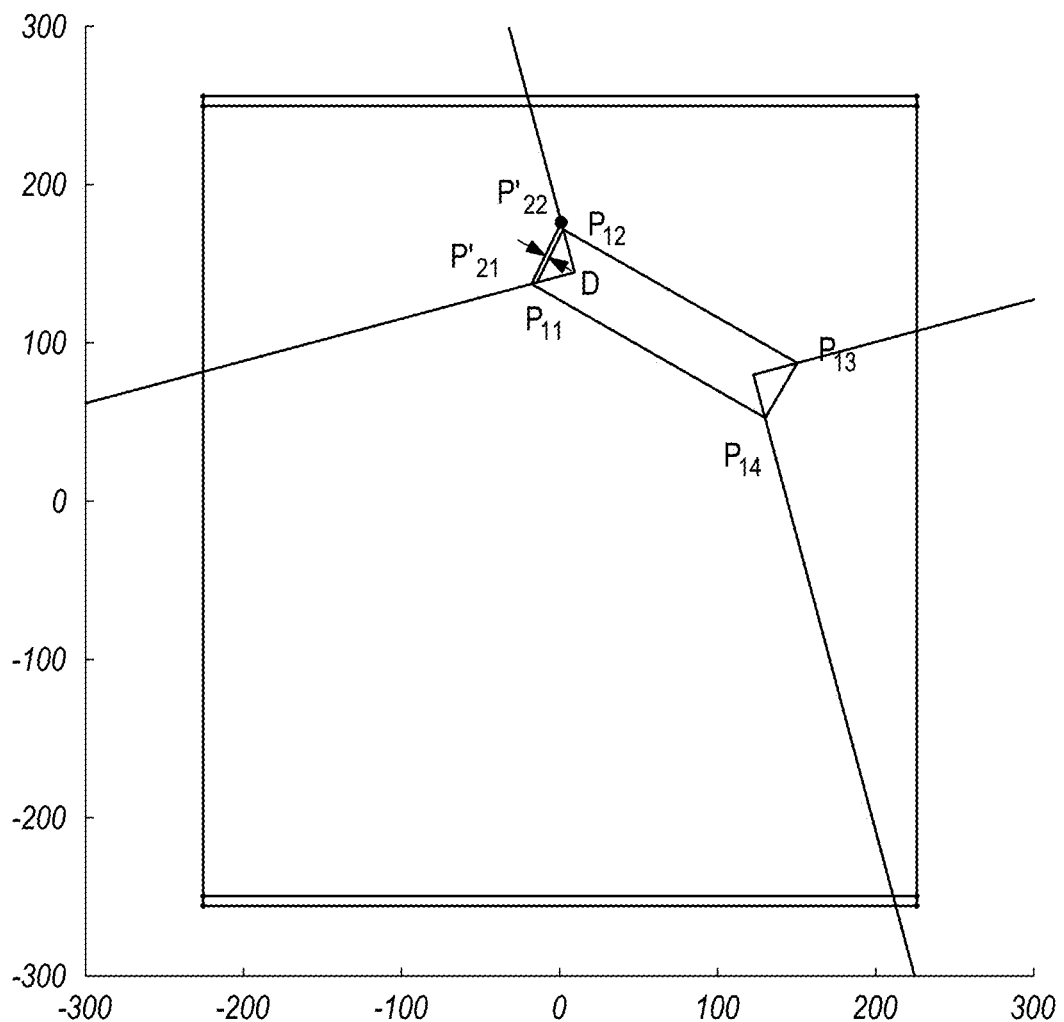

As shown in FIG. 8, distances between the linear portion connecting temporary vertices P'$_{21}$ and P'$_{22}$ and the linear portion between P$_{11}$ and P$_{12}$ are calculated. Since the linear portion connecting temporary vertices P'$_{21}$ and P'$_{22}$ and the linear portion between P$_{11}$ and P$_{12}$ may not be parallel, there are multiple distances between the two linear portions. At block 309, a determination is made as to whether the smallest distance D among the multiple distances between the two linear portions is less than or equal to TCCM. If it is determined at block 309 that the smallest distance D among the multiple distances is less than or equal to TCCM, then at block 311 the temporary distance D$_{p2to5}$ is increased by a predetermined amount and the above procedures of blocks 302 through 309 are repeated, including by using the equations (9)-(13) until the smallest distance D is greater than TCCM. The final result of VVM is set as the value for the vertex-to-vertex minimum.

If, on the other hand, it is determined at block 309 that the smallest distance D among the multiple distances is greater than TCCM, then at block 312 a planar antenna layout is generated by interconnecting the planar antenna vertices by way of respective straight linear portions to form multiple loops (e.g., N loops) that sequentially traverse each of the plurality of diagonal lines of the respective planar antenna.

Figure 11:
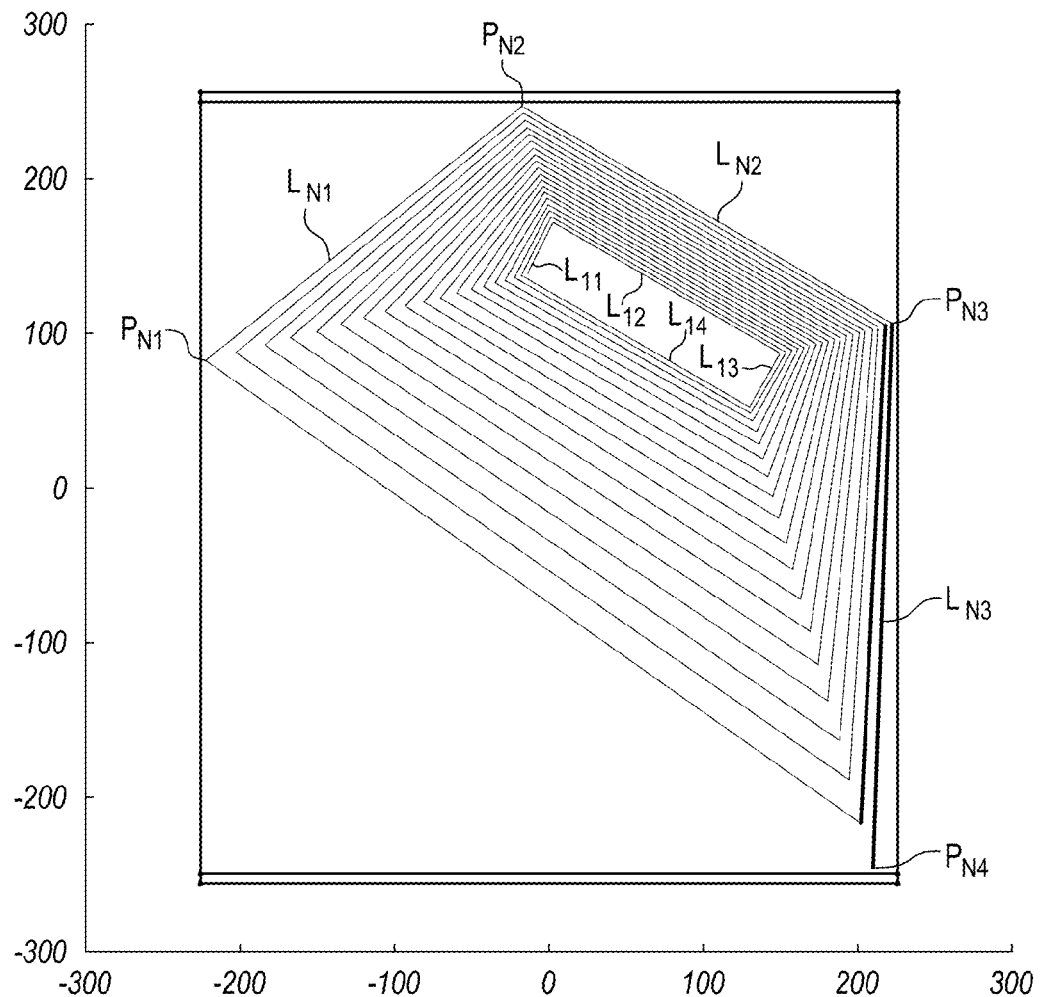

Each of the loops includes multiple straight linear portions and multiple planar antenna vertices, namely four straight linear portions and four planar antenna vertices, in a case where the seed shape is a seed rectangle. For example, the first loop of each loop antenna, such as the loop antenna shown in FIG. 11, includes four vertices (i.e., $P_{11}$, $P_{12}$, $P_{13}$, and $P_{14}$) and four linear portions (i.e., $L_{11}$ connecting between $P_{11}$ and $P_{12}$, $L_{12}$ connecting $P_{12}$ and $P_{13}$, $L_{13}$ connecting $P_{13}$ and $P_{14}$, and $L_{14}$ connecting $P_{14}$ and $P_{21}$); . . . the (N–1)-th loop includes four vertices (i.e., $P_{(N-1)1}$, $P_{(N-1)2}$, $P_{(N-1)3}$, and $P_{(N-1)4}$) and four linear portions (i.e., $L_{(N-1)\,1}$ connecting between $P_{(N-1)1}$ and $P_{(N-1)2}$, $L_{(N-1)2}$ connecting $P_{(N-1)2}$ and $P_{(N-1)3}$, $L_{(N-1)3}$ connecting $P_{(N-1)3}$ and $P_{(N-1)4}$, and $L_{(N-1)4}$ connecting $P_{(N-1)4}$ and $P_{N1}$) (for clarity, not labeled in FIG. 11); and the N-th loop includes four vertices (i.e., $P_{N1}$, $P_{N2}$, $P_{N3}$, and $P_{N4}$) and three linear portions (i.e., $L_{N1}$ connecting $P_{N1}$ and $P_{N2}$, $L_{N2}$ connecting $P_{N2}$ and $P_{N3}$, and $L_{N3}$ connecting $P_{N3}$ and $P_{N4}$). FIG. 11 shows a design for a loop antenna that includes a plurality of loops, which is designed according to the procedure 300.

At block 313, multiple additional straight linear portions are routed from at least two of the planar antenna vertices (in particular, from the two terminal antenna vertices located at the two ends, respectively, of the linear planar antenna layout) to one or more connector locations with respect to the coordinate system of the substrate. The multiple additional straight linear portions are added to the planar antenna layout. In embodiments where the procedure 300 is employed to design an antenna assembly that includes multiple planar antennas to be arranged on respective layers of a multiple-layer substrate, the planar antenna layouts may be routed to a single connector location, or to separate connector locations corresponding to each antenna, respectively, or to any combination of connectors.

Figure 12:
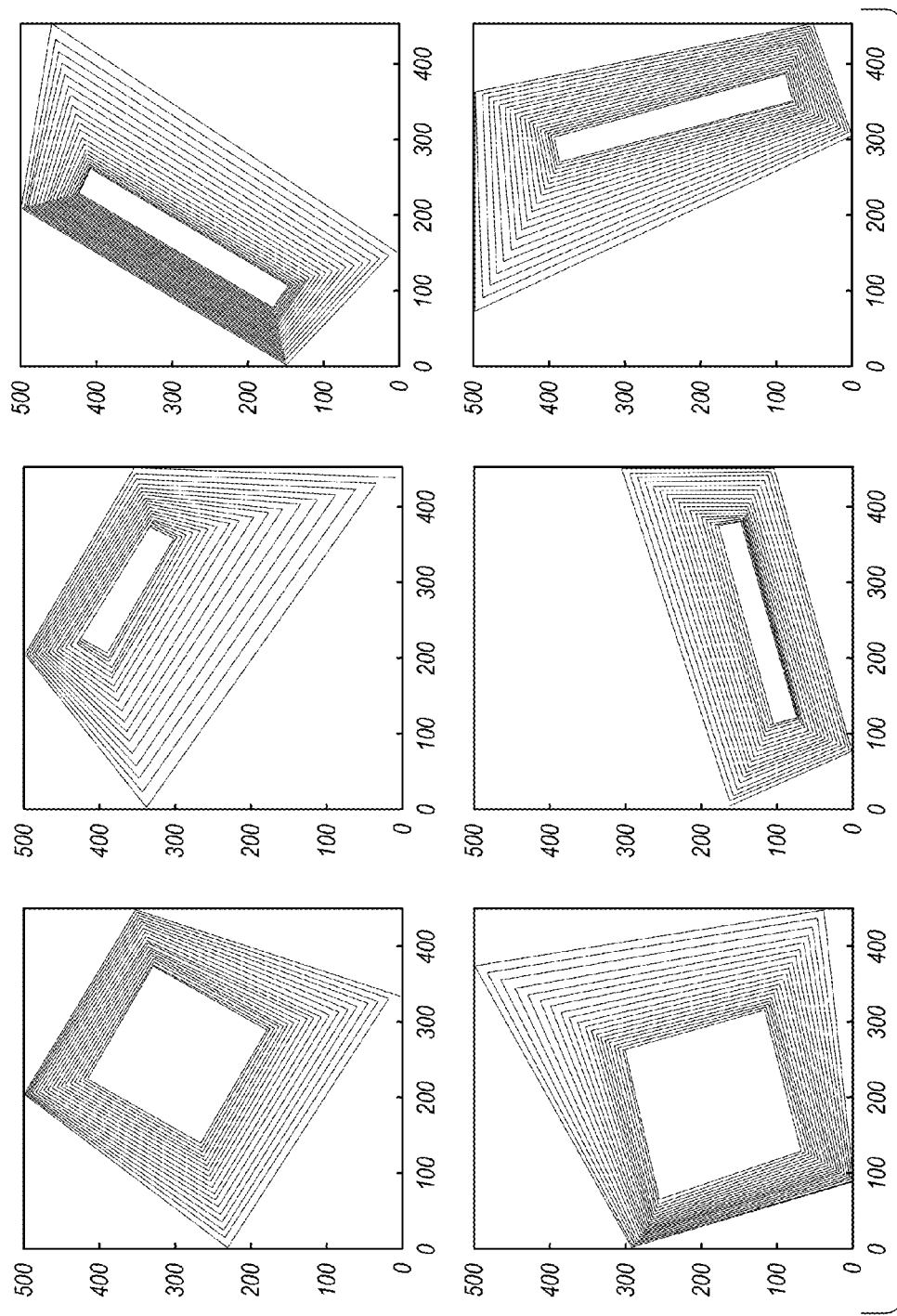
FIG. 12 is an illustration of multiple example antennas that may be designed according to the procedure of FIG. 3, in accordance with an embodiment of the present disclosure.

At block 314, the antenna index $i_{antenna}$ is compared to the number of antennas M of the antenna assembly to determine whether the procedures of block 302 through block 313 are to be repeated for additional antennas of the antenna assembly. If it is determined at block 314 that $i_{antenna}$ is less than the number of antennas M, then at block 315 $i_{antenna}$ is incremented by one to correspond to the next antenna (for example, the second antenna) of the M antennas of the antenna assembly. Then the procedures of block 302 through block 313 are repeated for that next antenna in the manner described above. FIG. 12 shows designs for six loop antennas, which can be designed in accordance with the procedure 300.

If, on the other hand, it is determined at block 314 that $i_{antenna}$ is equal to the number of antennas M, indicating that the procedures of block 302 through block 313 have been executed for each of the M antennas of the antenna assembly, then at block 316, which may be optional in some embodiments, data corresponding to the generated planar antenna layout is exported to a circuit board routing tool, a circuit board manufacturing tool, and/or an electromagnetic simulation tool.

In one example, by exporting the data corresponding to the generated planar antenna layout to the electromagnetic simulation tool at block 316, one or more electromagnetic fields that may be generated by the antennas of the antenna assembly may be simulated based on the exported data and on the superposition of multiple electromagnetic field components from each of the multiple straight linear portions of the planar antenna layout, respectively. For instance, each loop based on the seed shape can be expressed with a definite mathematical equation, such as a Cartesian equation or a parametric equation, such that the strength of an EM field generated by each loop can be calculated by the Biot-Savart-Laplace law at any point in space based on the mathematical equation. In other words, by virtue of geometrical and other aspects of the antenna assembly (such as the use of straight linear portions as the interconnections in the antennas of the antenna assembly), the need to generate and employ a detailed electromagnetic field mapping can be avoided by instead enabling an electromagnetic field mapping to be theoretically computed based on the characteristics of the antenna assembly. The computed electromagnetic field mapping can then be employed either alone or in conjunction with a more easily generated low-density electromagnetic field mapping obtained from measurements. In other words, the antenna assembly designed according to the procedure 300 can serve as the basis upon which to generate an accurate high-density theoretical electromagnetic field mapping for EMN, without having to use expensive measuring equipment and without having to perform time-consuming and laborious measurements.

As is apparent from the description herein, according to the procedure 300, an antenna assembly can be efficiently and designed in a repeatable manner based on a few design parameters and/or constraints, such as a seed shape, a number of loops, a TCCM, and/or the like. Each of the antennas of the designed antenna assembly can be printed, deposited, or fabricated on a respective substrate layer and can be used as the EM field generator 145 of the EMN system 100 of FIG. 1. Further, by virtue of employing straight linear portions to constitute the loop antennas, electromagnetic fields generated by each linear portion can be theoretically and accurately calculated using the Biot-Savart-Laplace law at any point in the EM volume.

Figure 13:
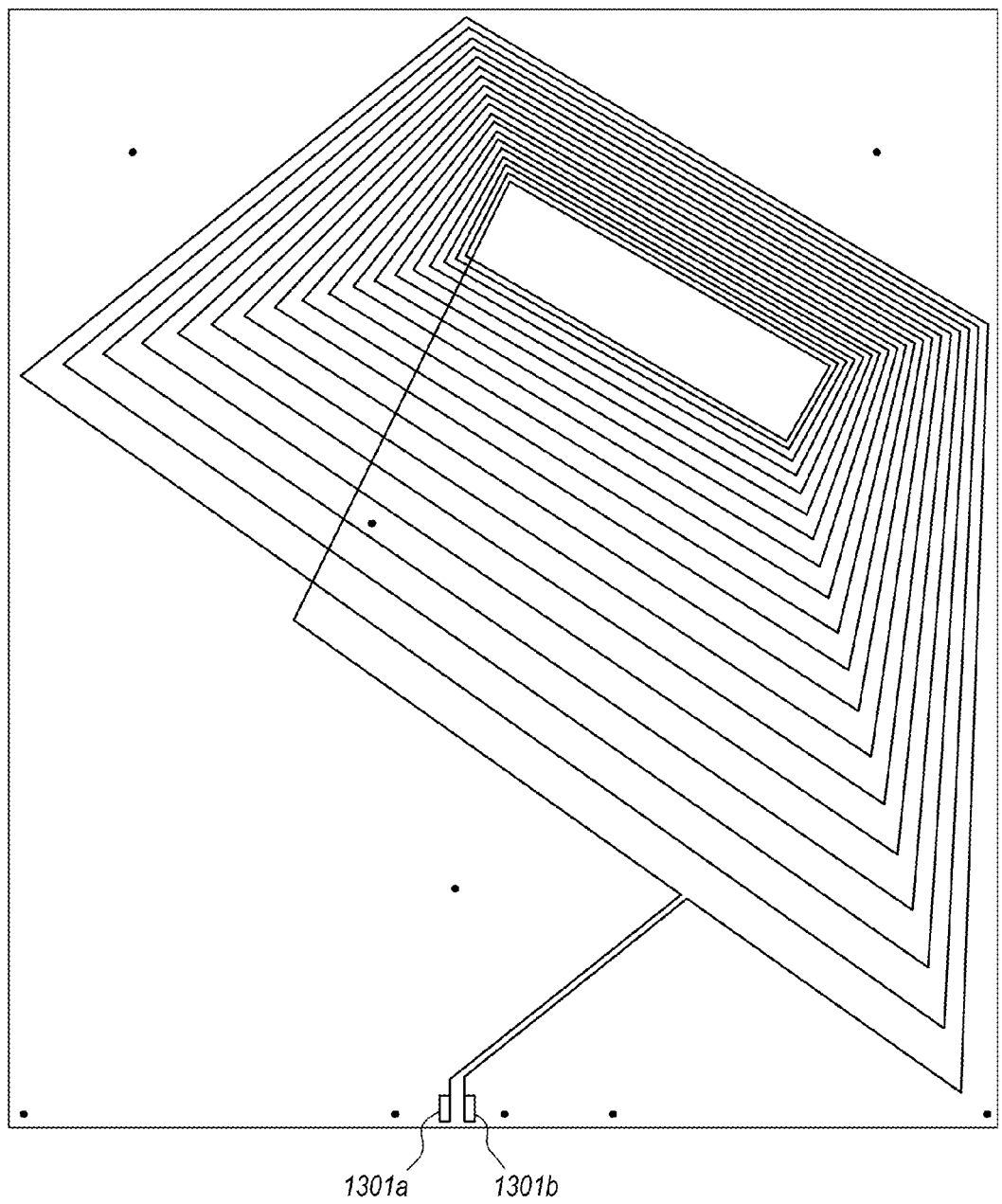
FIG. 13 shows an example design of a loop antenna layout trace placement, in accordance with an embodiment of the present disclosure.

FIG. 13 shows a graphical illustration of a loop antenna layout designed by the method 300 of FIG. 3. After connecting all the vertices, additional layout may be automatically generated based on a few design rules in place related to trace length and routing directionality. These rules may be specific to a PCB software program or design requirements. In an aspect, the antenna design made by the method 300 may be converted to a 2 dimensional DXF (Drawing eXchange Format) CAD file, which is then imported into Altium PCB layout software. PCB layout software is not limited to Altium PCB layout software but can be any software, which a person having ordinary skill in the art would readily appreciate and use.

Based on the design rules or design requirements of the software, vertices $P_{11}$ and $P_{N4}$ are electrically coupled to a connector 1301, which includes at least two conductors 1301a, 1301b of the loop antenna, respectively, and a full blueprint of the loop antenna is complete.

Upon completion of the design of the antenna assembly, an antenna is fabricated, based on the antenna assembly design, by depositing electrically conducting materials (e.g., silver or copper) on a substrate, as shown in FIG. 13. The antenna printed on the substrate includes structural and/or geometrical relationships between loops, which are described in detail below.

In an example aspect, vertices of the loop antenna can be grouped in four groups. The first group of vertices includes $P_{11}, P_{21}, \ldots,$ and $P_{N1}$, the second group of vertices includes $P_{12}, P_{22}, \ldots,$ and $P_{N2}$, the third group of vertices includes $P_{13}, P_{23}, \ldots,$ and $P_{N3}$, and the fourth group of vertices includes $P_{14}, P_{24}, \ldots,$ and $P_{N4}$. Because $V_{layout\_k}$ is different for each group, one group of vertices may be more densely distributed than the other groups of vertices. As shown in FIG. 13, vertices in the fourth group are more loosely distributed than vertices in the other groups, and the vertices in the second or third group are more densely distributed than vertices in the first and fourth groups.

In another aspect, the shortest distance between two corresponding linear portions (e.g., $L_{jk}$ and $L_{(j+1)k}$) increases as j increases. In other words, the distances between two adjacent corresponding linear portions are increasing in a direction from the innermost linear portion to the corresponding outermost linear portion. Based on this structural and/or geometrical relationship among loops and vertices, the loop antenna can cover the substrate as much as possible while maintaining such a relationship.

In an embodiment, after connecting the vertices with linear portions, another safety measure may be employed to confirm that all the requirements are satisfied in the antenna design. For example, shortest distances between two adjacent corresponding linear portions may be calculated again. In a case when there are any two adjacent corresponding linear portions, between which the shortest distance is not greater than TCCM, the procedure 300 can be repeated with a different minimum vertex to vertex distance VVM.

In an aspect, the design procedure 300 can enable maintaining substantially the same inductance of each loop antenna because the inductance is defined based at least in part on the antenna geometry. The resistance of the loop antenna may vary with copper thickness on each layer. Thus, in order to ensure that the antenna assembly maintains the intended copper thickness, two additional layers (one on the top and the other on the bottom) are added. With these extra layers, the plating processing for the vias would not add copper to the antenna layers on the internal layers. Thus, the copper thickness may depend only on the core material used and copper weight selected, initially. In another aspect, the PCB design may contain more than a single via for each current carrying path to minimize series resistance and increase the robustness of each current path. By having more vias, the resistance can be predicted and automatically calculated with high accuracy based on the antenna geometry and controlled copper thickness.

Figure 14:
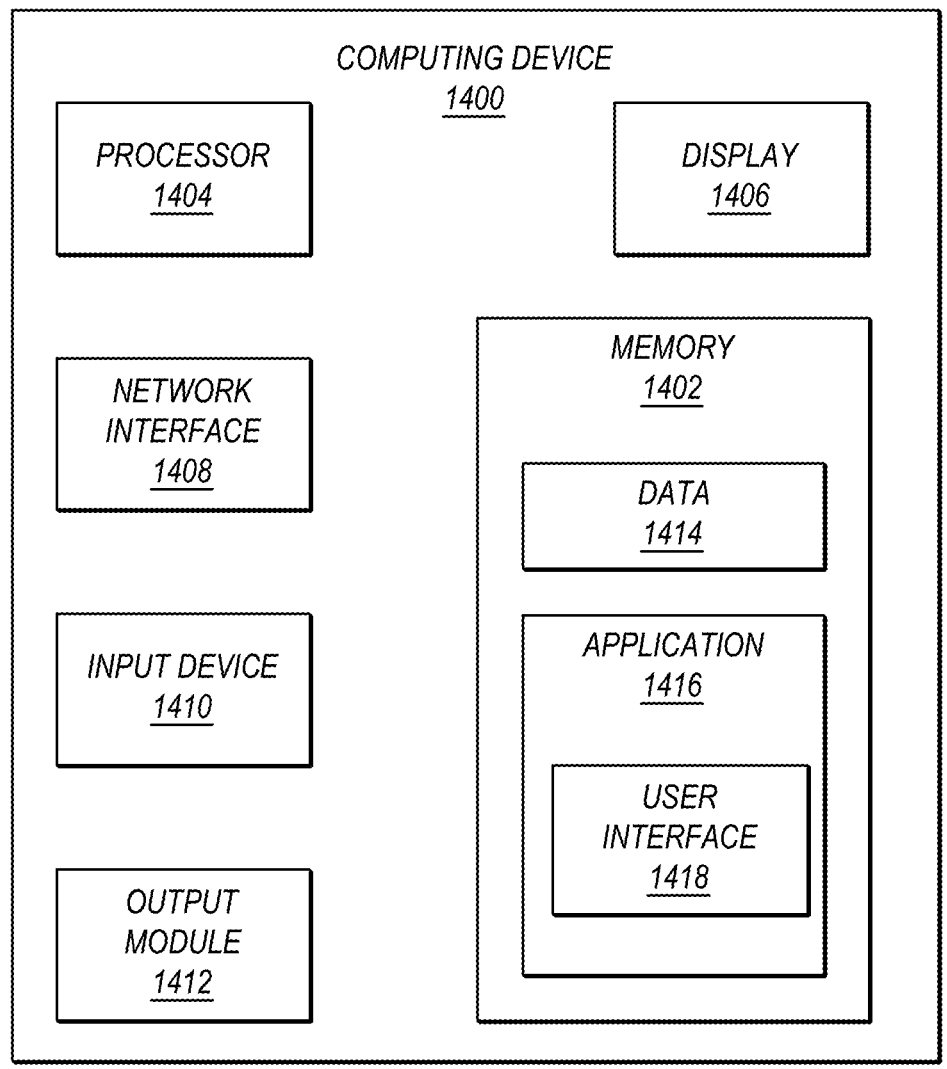
FIG. 14 is a block diagram of an example computing device for use in various embodiments of the present disclosure.

Turning now to FIG. 14, there is shown a block diagram of a computing device 1400, which can be used as the EMN system 100, the control workstation 102, the tracking device 160, and/or a computer performing the procedure 300 of FIG. 3. The computing device 1400 may include one or more of each of the following components: a memory 1402, a processor 1404, a display 1406, network interface controller 1408, an input device 1410, and/or an output module 1412.

The memory 1402 includes any non-transitory computer-readable storage media for storing data and/or software that is executable by the processor 1404 and which controls the operation of the computing device 1400. In an embodiment, the memory 1402 may include one or more solid-state storage devices such as flash memory chips. Alternatively, or in addition to the one or more solid-state storage devices, the memory 1402 may include one or more mass storage devices connected to the processor 1404 through a mass storage controller (not shown in FIG. 14) and a communications bus (not shown in FIG. 14). Although the description of computer-readable media contained herein refers to a solid-state storage, it should be appreciated by those skilled in the art that computer-readable storage media can be any available media that can be accessed by the processor 1404. That is, examples of computer readable storage media include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 1400.

The memory 1402 may store application 1416 and/or data 1414. The application 1416 may, when executed by the processor 1404, cause the display 1406 to present user interface 1418 on the display 1406.

The processor 1404 may be a general purpose processor, a specialized graphic processing unit (GPU) configured to perform specific graphics processing tasks while freeing up the general purpose processor to perform other tasks, a programmable logic device such as a field programmable gate array (FPGA) or complex programmable logic device (CPLD), and/or any number or combination of such processors or devices configured to work independently or cooperatively.

The display 1406 may be touch-sensitive and/or voice-activated, enabling the display 1406 to serve as both an input and output device. Alternatively, a keyboard (not shown), mouse (not shown), or other data input devices may be employed.

The network interface 1408 may be configured to connect to a network, such as a local area network (LAN) including a wired network and/or a wireless network, a wide area network (WAN), a wireless mobile network, a Bluetooth network, and/or the Internet. For example, the computing device 1400 may receive design requirements and predetermined variables and perform the procedure 300 of FIG. 3 to design an antenna assembly. The computing device 1400 may receive updates to its software, for example, application 1416, via the network interface controller 1408. The computing device 1400 may also display notifications on the display 1406 that a software update is available.

In another aspect, the computing device 1400 may receive computed tomographic (CT) image data of a patient from a server, for example, a hospital server, Internet server, or other similar servers, for use during surgical planning. Patient CT image data may also be provided to the computing device 1400 via a removable memory (not shown in FIG. 14).

Input device 1410 may be any device by means of which a user may interact with the computing device 1400, such as, for example, a mouse, keyboard, foot pedal, touch screen, and/or voice interface.

Output module 1412 may include any connectivity port or bus, such as, for example, parallel ports, serial ports, universal serial busses (USB), or any other similar connectivity port known to those skilled in the art.

The application 1416 may be one or more software programs stored in the memory 1402 and executed by the processor 1404 of the computing device 1400. During a design phase for loop antennas, one or more software programs in the application 1416 may be loaded from the memory 1402 and executed by the processor 1404 to automatically design loop antennas, given certain parameters and/or constraints, such as seed shape information, the number of loops in each loop antenna, and/or the like. In some embodiments, during a planning phase, one or more programs in the application 1416 guides a clinician through a series of steps to identify a target, size the target, size a treatment zone, and/or determine an access route to the target for later use during the navigation or procedure phase.

In some other embodiments, one or more software programs in the application 1416 may be loaded on computing devices in an operating room or other facility where surgical procedures are performed, and is used as a plan or map to guide a clinician performing a surgical procedure, but without any feedback from the medical device used in the procedure to indicate where the medical device is located in relation to the plan.

The application 1416 may be installed directly on the computing device 1400, or may be installed on another computer, for example a central server, and opened on the computing device 1400 via the network interface 1408. Application 1416 may run natively on the computing device 1400, as a web-based application, or any other format known to those skilled in the art. In some embodiments, the application 1416 will be a single software program having all of the features and functionality described in the present disclosure. In other embodiments, the application 1416 may be two or more distinct software programs providing various parts of these features and functionality. For example, the application 1416 may include one software program for automatically designing loop antennas, another one for converting the design into a CAD file, and a third program for PCB layout software program. In such instances, the various software programs forming part of the application 1416 may be enabled to communicate with each other and/or import and export various data including settings and parameters relating to the design of the loop antennas. For example, a design of a loop antenna generated by one software program may be stored and exported to be used by a second software program to convert into a CAD file, and the converted file may be also stored and exported to be used by a PCB layout software program to complete a blueprint of the loop antenna.

The application 1416 may communicate with a user interface 1418 which generates a user interface for presenting visual interactive features to a user, for example, on the display 1406 and for receiving input, for example, via a user input device. For example, user interface 1418 may generate a graphical user interface (GUI) and output the GUI to the display 1406 for viewing by a user.

In a case that the computing device 1400 may be used as the EMN system 100, the control workstation 102, or the tracking device 160, the computing device 1400 may be linked to the monitoring device 130, thus enabling the computing device 1400 to control the output on the monitoring device 130 along with the output on the display 1406. The computing device 1400 may control the monitoring device 130 to display output which is the same as or similar to the output displayed on the display 1406. For example, the output on the display 1406 may be mirrored on the monitoring device 130. Alternatively, the computing device 1400 may control the monitoring device 130 to display different output from that displayed on the display 1406. For example, the monitoring device 130 may be controlled to display guidance images and information during the surgical procedure, while the display 1406 is controlled to display other output, such as configuration or status information of an electrosurgical generator (not shown in FIG. 1).

The application 1416 may include one software program for use during the planning phase, and a second software program for use during the navigation or procedural phase. In such instances, the various software programs forming part of application 1416 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. An antenna assembly for radiating at least one electromagnetic field for electromagnetic navigation, the antenna assembly comprising:
   a substrate; and
   a planar antenna including a trace deposited on the substrate and arranged in a plurality of loops,
   wherein respective distances between any two adjacent loops of the plurality of loops progressively increase in a direction from an innermost loop of the plurality of loops to an outermost loop of the plurality of loops.

2. The antenna assembly according to claim 1, wherein each of the plurality of loops includes a plurality of straight linear portions and a plurality of vertices.

3. The antenna assembly according to claim 2, wherein each of the plurality of loops includes four straight linear portions and four vertices.

4. The antenna assembly according to claim 3, wherein each of the plurality of vertices is disposed along one of four diagonal lines that bisect four respective vertices of a seed rectangle corresponding to the planar antenna.

5. The antenna assembly according to claim 1, further comprising:
   a connector having at least two terminals,
   wherein the trace has two ends that are coupled to the two terminals, respectively.

6. The antenna assembly according to claim 1, further comprising:
   a plurality of planar antennas,
   wherein each of the plurality of planar antennas includes a respective trace deposited on the substrate and arranged in a respective plurality of loops, and
   wherein, for each of the plurality of planar antennas, respective distances between adjacent loops of the respective plurality of loops increase in a direction from an innermost loop of the respective plurality of loops to an outermost loop of the respective plurality of loops of the respective planar antenna.

7. The antenna assembly according to claim 6, wherein the substrate includes a plurality of layers and the planar antenna and each of the plurality of planar antennas is deposited on a respective layer of the plurality of layers.

8. The antenna assembly according to claim 6, wherein the planar antenna and each of the plurality of planar antennas each include a same number of loops.

9. The antenna assembly according to claim 6, wherein each of the loops of each of the plurality of planar antennas includes a plurality of straight linear portions and a plurality of vertices.

10. The antenna assembly according to claim 6, wherein the planar antenna and the plurality of planar antennas have a plurality of centroids, respectively, with respect to a plane of the substrate that are disposed in respective positions that are distinct from one another.

* * * * *